US006916905B2

(12) United States Patent
Lazarus et al.

(10) Patent No.: US 6,916,905 B2
(45) Date of Patent: Jul. 12, 2005

(54) DMT-TIC DI-AND TRI-PEPTIDIC DERIVATIVES AND RELATED COMPOSITIONS AND METHODS OF USE

(75) Inventors: Lawrence H. Lazarus, Durham, NC (US); Severo Salvadori, Ferrara (IT)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 454 days.

(21) Appl. No.: 10/037,358

(22) Filed: Dec. 21, 2001

(65) Prior Publication Data

US 2002/0161189 A1 Oct. 31, 2002

Related U.S. Application Data

(63) Continuation-in-part of application No. 09/814,558, filed on Mar. 22, 2001, now Pat. No. 6,753,317.
(60) Provisional application No. 60/192,128, filed on Mar. 24, 2000.

(51) Int. Cl.[7] .................................................. C07K 5/08
(52) U.S. Cl. ........................ 530/331; 530/330; 514/18; 514/19; 546/146; 546/150; 562/553
(58) Field of Search ............................ 514/18, 19, 187; 546/146, 150; 562/553; 530/330, 331

(56) References Cited

U.S. PATENT DOCUMENTS

| 5,780,589 A | 7/1998 | Lazarus et al. ............. 530/331 |
| 5,811,400 A | 9/1998 | Schiller ....................... 514/19 |

OTHER PUBLICATIONS

Lazarus et al., International Symposium on Peptide Chem & Biol, Changchung, PRC (1999).*
Abrash et al., Biochemistry, 2(5):947–953, Sep.–Oct. (1963).
Arakawa et al., Transplantation, 53(4): 951–953, Apr. (1992).
Arakawa et al., Transplantation Pro., 24(2):696–697, Apr. (1992).
Arakawa et al., Transplantation Pro., 25(1):738–740, Feb. (1993).
Balboni et al., Biol. Chem., 378:19–29, Jan. (1997).
Borch et al., J. Org. Chem., 37(10):1673–1674 (1972).
Bryant et al., Biol. Chem, 378:107–114, Feb. (1997).
Bryant et al., Trends in Pharmacol. Sci., 18: 42–46 (1998).
Callaghan et al., J. Biol. Chem., 268(21):16059–16064, Jul. 25, (1993).
Capasso et al., Int. J. Peptide Protein Res., 45:567–573 (1995).
Carpenter et al., J. Am. Chem. Soc., 116(19):8450–8458 (1994).
Chappell, Lancet, 343:556, Mar. 5, (1994).
Crabb et al., J. Chem. Soc., Perkins Transactions II, 370–378 (1977).
Crescenzi et al., Eur. J. Biochem., 247:66–73 (1997).
Dygos et al., Synthesis, 741–743, Aug. (1992).
Ermishc et al., Phys. Rev., 73(3):489–527, Jul. (1993).
Flippen–Anderson et al., J. Peptide Res., 49:384–393 (1997).
Ford et al., Cancer Research, 50:1748–1756, Mar. 15 (1990).
Froehlich et al., Alcohol Clin. Exp. Res., 20(8):181A–186A, Nov. Supp. (1996).
Guerrini et al., Bioorg. Med. Chem., 6:57–62 (1998).
Hayashi et al., Chem. Pharm. Bull., 31(1):312–314 (1983).
House et al., Neurosci. Lett., 198:119–122 (1995).
Jones et al., J. of Pharm. Exp. Thera., 262(2):638–645 (1992).
Kertész et al., J. Labelled Cpd. and Radiopharm., XLI:1083–1091 (1998).
Lazarus et al., J. Biol. Chem., 264(1):354–362, Jan. 5 (1989).
Lazarus et al., Biochem. Biophys. Res. Comm., 178(1):110–115, Jul. 15 (1991).
Lazarus et al., Drug Devel. Today, 3(6):284–294, Jun. 6 (1998).
Lensing et al., Neuropsychobiology, 31:16–23 (1995).
Linner et al., Eur. J. of Pharmacol., 354:R3–R5 (1998).
Marsden et al., Int. J. Peptide Protein Res., 41:313–316 (1993).
Matthes et al., Nature, 383:819–823, Oct. 31 (1996).
Menkens et al., Eur. J of Pharmacol., 219:345–346 (1992).
Mosberg et al., Letters in Peptide Science, 1:69–72 (1994).
Nogae et al., Biochem. Pharmacol., 38(3):519–527 (1989).
Pearce et al., Proc. Natl. Acad. Sci. USA, 86:5128–5132, Jul. (1989).
Portoghese et al., Eur. J. Pharmacol., 146:185–186 (1988).
Ramu et al., Int. J. Cancer, 43:487–491 (1989).
Sagan et al., Biochem. Biophys. Res. Commun., 187(3):1203–1210, Sep. 30 (1992).

(Continued)

*Primary Examiner*—Jon Weber
*Assistant Examiner*—David Lukton
(74) *Attorney, Agent, or Firm*—Leydig, Voit & Mayer, Ltd.

(57) ABSTRACT

A compound of formula:

wherein X is a spacer comprising one or more amino acid residues and Y comprises an aromatic group and related compositions and methods of use.

10 Claims, 2 Drawing Sheets

OTHER PUBLICATIONS

Salvadori, Mol. Med. 1(6):678–689, Sep. (1995).
Salvadori, J. Med. Chem., 42:5010–5019 (1999).
Schiller et al., Proc. Natl. Acad. Sci. USA, 89:11871–11875, Dec. (1992).
Schiller et al., Peptides: Chemistry, Structure and Biology; Proceedings of the Thirteenth American Peptide Symposium, pp. 483–486, Jun. 20–25 (1993), Edmonton, Alberta, Canada, ESCOM.
Schiller et al., J. Med. Chem., 36(21):3182–3187 (1993).
Schinkel, et al., J. Clin. Invest., 97(11):2517–2524, Jun. (1996).
Schinkel, Intern. J. Clin. Pharm. Therapeutics, 36(1):9–13 (1998).
Temussi et al., Biochem. Biophys. Res. Commun., 198(3):933–939, Feb. 15 (1994).
Jonker et al., Br. J of Pharmacol., 127:43–50 (1999).
Zamora et al., Mol. Pharmacol., 33:454–462 (1988).

* cited by examiner

23

24

25

26

27

28

DMT-TIC DI-AND TRI-PEPTIDIC DERIVATIVES AND RELATED COMPOSITIONS AND METHODS OF USE

CROSS-REFERENCE TO RELATED PATENT APPLICATION

This patent application is a "continuation-in-part" of U.S. patent application Ser. No. 09/814,558, filed Mar. 22, 2001 now U.S. Pat. No. 6,753,317, which claims the benefit of U.S. Provisional Patent Application No. 60/192,128, which was filed on Mar. 24, 2000.

TECHNICAL FIELD OF THE INVENTION

The present invention relates to di- and tri-peptidic derivatives comprising the pharmacophore H-Dmt-Tic-X-Y, wherein X is a spacer comprising one or more amino acid residues, and Y comprises an aromatic group, which produce selective bifunctional opioid ligands for the $\delta$ and $\mu$ opioid receptors. The present invention also relates to compositions thereof and methods of use therefor in the antagonism and agonism of $\delta$ and $\mu$ opioid receptors.

BACKGROUND OF THE INVENTION

Endogenous opioids are believed to be involved in the modulation of pain perception, in mood and behavior, learning and memory, diverse neuroendocrine functions, immune regulation and cardiovascular and respiratory function. Opioids also have a wide range of therapeutic utilities, such as treatment of opiate and alcohol abuse, neurological diseases, neuropeptide or neurotransmitter imbalances, neurological and immune system dysfunctions, graft rejections, pain control, shock and brain injuries.

There are believed to be three types of opiate receptors, namely $\delta$, $\kappa$ and $\mu$. Genes encoding these three main receptor types now have been cloned. Sequencing of the cloned opioid receptor genes has revealed a substantial degree of amino acid homology between different receptor types (Meng et al., *PNAS USA* 90: 9954–9958 (1993); Thompson et al., *Neuron* 11: 903–913 (1993); Evans et al., *Science* 258: 1952–1955 (1992); and Kieffer et al., *PNAS USA* 89: 12048–12052 (1992)), which explains the tendency of opioid receptor ligands, even those reported to be selective, to bind to more than one type of opioid receptor. Based on differences in the binding profiles of natural and synthetic ligands, subtypes of opioid receptors have been suggested, including $\mu$1 and $\mu$2 (Pasternak et al., *Life Sci.* 38: 1889–1898 (1986)) and $\kappa$1 and $\kappa$2 (Zukin et al., *PNAS USA* 85: 4061–4065 (1988)). Different subtypes of a given type of opioid receptor may co-exist in a single cell (Evans et al. (1992), supra; and Kieffer et al. (1992), supra).

The $\mu$ opioid receptor in the brain appears to mediate analgesia (Kosterlitz et al., *Br. J. Pharmacol.* 68: 333–342 (1980)). It is also believed to be involved with other undesirable effects, such as respiratory depression (Ward et al., *Soc. Neurosci. Symp.* 8: 388 (abstract) (1982)), suppression of the immune system (Plotnikoff et al., *Enkephalins and Endorphins: Stress and the Immune System*, Plenum Press, NY (1986); Yahya et al., *Life Sci.* 41: 2503–2510 (1987)) and addiction (Roemer et al., *Life Sci.* 27: 971–978 (1981)). Its side effects in the periphery include inhibition of intestinal motility (Ward et al., *Eur. J. Pharmacol.* 85: 163–170 (1982)) and secretion in the small intestine (Coupar, *Br. J. Pharmacol.* 80: 371–376 (1983)).

$\delta$-opioid receptors also mediate analgesic but are not involved in addiction. They may have an indirect role in immune suppression.

There appears to be a single binding site for agonists and antagonists in the ligand-binding domain of $\delta$ receptors. Thus, the "message domain" of $\delta$-agonists and $\delta$-antagonists probably presents a similar low energy conformer in order to fit the receptor cavity. The minimum size of that "message domain" constitutes the dimensions of a dipeptide (Temussi et al., *Biochem. Biophys. Res. Commun.* 198: 933–939 (1994); Mosberg et al., *Lett. Pept. Sci.* 1: 69–72 (1994); and Salvadori et al., *J. Med. Chem.* 42: 3100–3108 (1997)), which has a specific spatial geometry in solution (Bryant et al., *Trends Pharmacol. Sci.* 18: 42–46 (1998); Bryant et al., *Biol. Chem.* 378: 107–114 (1997); Crescenzi et al., *Eur. J. Biochem.* 247: 66–73 (1997); and Guerrini et al., *Bioorg. Med. Chem.* 6: 57–62 (1998)) as seen in the crystallographic evidence for TIPP analogues (Flippen-Anderson et al., *J. Pept. Res.* 49: 384–393 (1997)) and N,N(Me)$_2$-Dmt-Tic-OH.

The Dmt-Tic pharmacophore represents a distinct class of $\delta$-opioid antagonists (Salvadori et al., *Mol. Med.* 1: 678–689 (1995); Bryant et al. (1998), supra; and Lazarus et al., *Drug Dev. Today* 1998: 284–294). Observations of differences between the $\delta$ opioid receptor binding of Dmt-Tic peptides and their Tyr-Tic cognates (Salvadori et al. (1995), supra; Lazarus et al. (1998), supra; and Lazarus et al., *Int'l Symp. on Peptide Chem. and Biol.*, Changchung, PRC (1999)) indicates that Dmt assumes a predominant role in the alignment or anchoring of the peptide within $\delta$, $\mu$ and $\kappa$ opioid receptor binding sites (Bryant et al. (1998), supra; and Bryant et al. (1997), supra; Crescenzi et al. (1997), supra; and Guerrini et al. (1998), supra) or affects the conformation of the dipeptide antagonists in solution (Bryant et al. (1997), supra; and Crescenzi et al. (1997), supra). Furthermore, observations of differences between the spectra of activity exhibited by the Tyr-Tic cognates of certain Dmt-Tic peptides (Schiller et al., *PNAS USA* 89: 11871–11875 (1992); Schiller et al., *J. Med. Chem.* 36: 3182–3187 (1993); Schiller et al., *Peptides* Hodges and Smith, eds., ESCOM (1994); pp. 483–486; Temussi et al. (1994), supra; Mosberg et al. (1994), supra; Salvadori et al. (1995), supra; Lazarus et al. (1998), supra; and Lazarus et al. (1999), supra) and the corresponding Dmt-Tic peptides suggests that the C-terminal "address" portion of the peptide can influence the "message domain."

Recently, cyclic peptides and di- and tri-peptides comprising the pharmacophore Dmt-Tic have been developed and have been shown to exhibit high selectivity, affinity and potency for the $\delta$-opioid receptor. Such peptides have been shown to function as agonists, partial agonists, antagonists, partial antagonists or mixed antagonists/agonists for opioid receptors (see Lazarus et al., U.S. Pat. No. 5,780,589, and Schiller, U.S. Pat. No. 5,811,400).

A variety of modifications to the Tic residue differentially changes receptor selectivity, including alterations in its electronic configuration and chirality, as well as its replacement by heteroaliphatic/heteroaromatic nuclei or D-Phe (Santagada et al., *Med. Chem. Lett.*, 10, 2745–2748 (2000); Pagé et al., *Bioorg. Med. Chem. Lett.*, 10, 167–170 (2000); Salvadori et al., *Mol. Med.*, 1: 678–689 (1995); Balboni et al., *Peptides*, 21: 1663–1671 (2000); and Capasso et al., *FEBS Lett.*, 417: 141–144 (1997)). Changes wrought by altering the distance to a third aromatic center ("Y") at the C-terminus by an interposed sequence, a spacer ("X"), induces profound changes in the affinity, selectivity and bioactivity of a ligand (Capasso et al., *FEBS Lett.*, 417: 141–144 (1997); Salvadori et al., *J. Med. Chem.*, 42: 5010–5019 (1999); Pagé et al., *J. Med. Chem.*, 44: 2387–2390 (2001)).

The uniqueness of the δ receptor has led to the use of moderately δ-selective alkaloid antagonists in clinical trials, such as for the amelioration of the effects of alcoholism (Froehlich et al., *Alcohol. Clin. Exp. Res.* 20: A181–A186 (1996)), the treatment of autism (Lensing et al., *Neuropsychobiol.* 31: 16–23 (1995)), and Tourette's syndrome (Chappell, *Lancet* 343: 556 (1994)). The δ-opiate antagonist naltrindole (Portoghese et al., *Eur. J. Pharm.* 146: 185–186 (1998)) has been shown to inhibit the reinforcing properties of cocaine (Menkens et al., *Eur. J. Pharm.* 219: 346–346 (1992)), to moderate the behavioral effects of amphetamines (Jones et al., *J. Pharmacol. Exp. Ther.* 262: 638–645 (1992)), and to suppress the immune system (Jones et al. (1992), supra) for successful organ transplantation (House et al., *Neurosci. Lett.* 198: 119–122 (1995)) in animal models (Arakawa et al., *Transplant Proc.* 24: 696–697 (1992); Arakawa et al., *Transplant* 53: 951–953 (1992); and Arakawa et al., *Transplant. Proc.* 25: 738–740 (1993)). The same effects also have been shown for 7-benzylspiroindanylnaltrexone (Lipper et al., *Eur. J. Pharmacol.* 354: R3–R5 (1998)).

The intractable membrane barriers, such as the blood-brain barrier (BBB), must be circumvented in order for peptide antagonists to express activity in vivo (Ermisch et al., *Physiol. Rev.* 73: 489–527 (1993)). The requisite physicochemical properties of compounds capable of passing through this barrier include low molecular weight (<800 Da) and high octanol-water coefficient characteristics.

In view of the above, the present invention seeks to provide more potent δ-opioid antagonists and δ-opioid antagonists with high dual binding affinity and biological activity toward δ-opioid and μ-opioid receptors.

In addition to the above, one of the major chemical determinants for the inhibition of hMDR-1 involves the presence of strong hydrophobic substituents necessary for lipid solubility (Ford et al., *Cancer Res.* 50: 1748–1756 (1990); Zamora et al., *Mol. Pharmacol.* 33: 454–462 (1988); and Nogae et al., *Biochem. Pharmacol.* 38: 519–527 (1989)) as constituted by saturated and aromatic rings, as well as a tertiary nitrogen (Zamora et al. (1988), supra; Ramu et al., *Int. J. Cancer* 43: 487–491 (1989); and Pearce et al., *PNAS USA* 86: 5128–5133 (1989)). In addition to a role in drug resistance, the human Pgp-1 protein is expressed in a variety of normal human tissues and plays an important physiological role in maintenance of the BBB (Schinkel et al., *J. Clin. Invest.* 97: 2517–2524 (1996); Schinkel et al., *Int. J. Clin. Pharmacol. Ther.* 36: 9–13 (1998); and Jonker et al., *Br. J. Pharmacol.* 127: 43–50 (1999)). In the BBB, Pgp activity in apical membranes of the capillary endothelial cells functions to at least partially exclude a wide variety of hydrophobic toxicants from the brain (Zamora et al. (1988), supra; Schinkel et al. (1996), supra; and Jonker et al., *Br. J. Pharmacol.* 127: 43–50 (1999)). These include some drugs with central nervous system activities, such as certain opiate alkaloids and analogues thereof (Callaghan et al., *J. Biol. Chem.* 268: 16059–16064 (1993)). Thus, the present invention also seeks to provide inhibitors of hMDR-1.

These and other objects of the present invention, as well as additional inventive features, will be apparent to the ordinarily skilled artisan from the detailed description provided herein.

BRIEF SUMMARY OF THE INVENTION

The present invention provides a compound of formula:

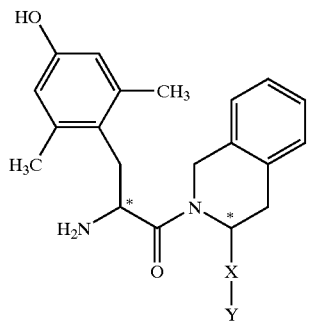

wherein X is a spacer comprising one or more amino acid residues, and Y comprises an aromatic compound.

More particularly, the present invention provides a compound of formula:

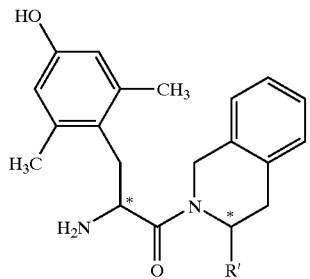

wherein R' is selected from the group consisting of

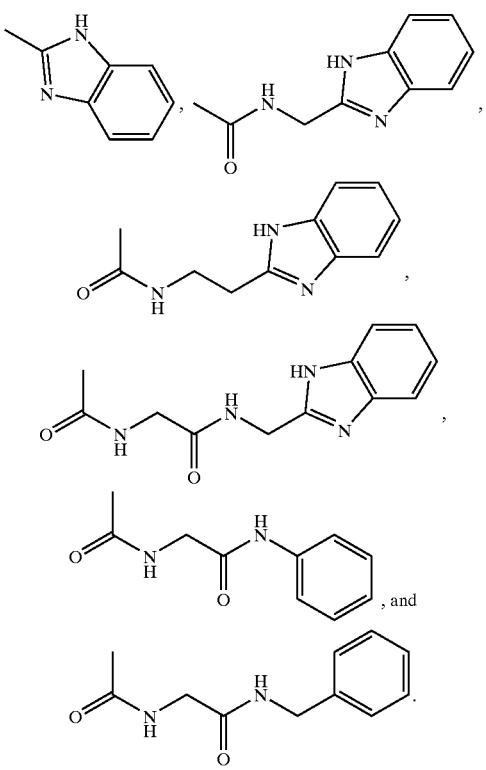

Also provided by the present invention is a composition comprising at least one the above-described compounds and a carrier.

The present invention further provides methods of treatment. In one embodiment, a method of treating a mammal in need of an antagonist of a δ-opioid receptor is provided. The method comprises administering at least one compound of formula:

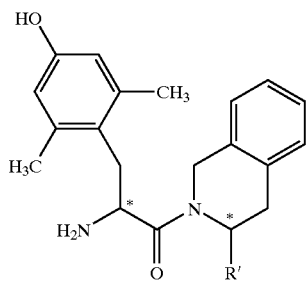

wherein R' is

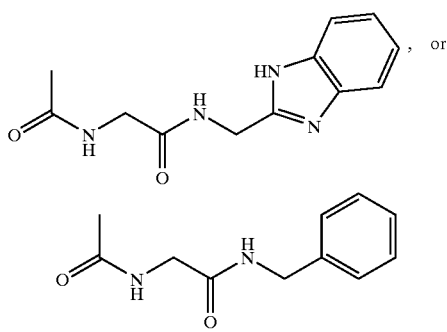

in an amount that antagonizes a δ-opioid receptor in the mammal.

The present invention further provides a method of treating a mammal in need of an agonist of a δ-opioid receptor. The method comprises administering at least one compound of formula:

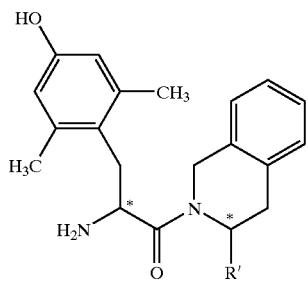

wherein R' is

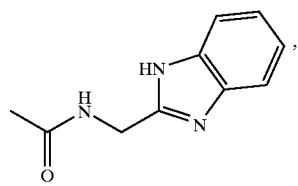

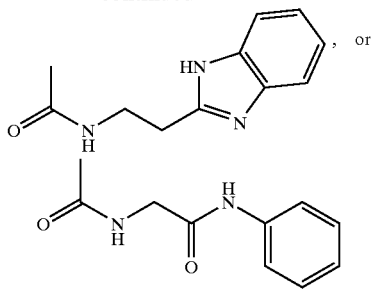

in an amount that agonizes a δ-opioid receptor in said mammal.

In yet another embodiment, the present invention provides a method of treating a mammal in need of an agonist of a μ-opioid receptor. The method comprises administering at least one compound of formula:

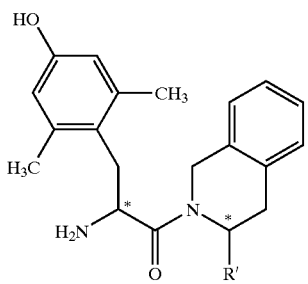

wherein R' is

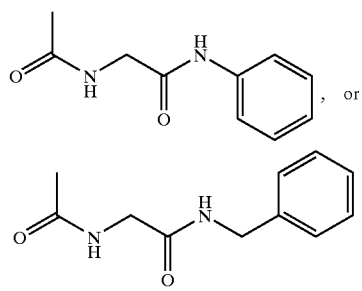

in an amount that agonizes a μ-opioid receptor in the mammal.

DETAILED DESCRIPTION OF THE INVENTION

The present invention provides a compound of formula:

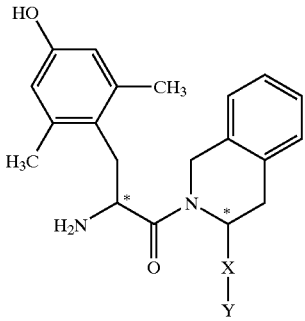

wherein X is a spacer comprising one or more amino acid residues, and Y comprises an aromatic compound.

The present invention further provides a compound of formula:

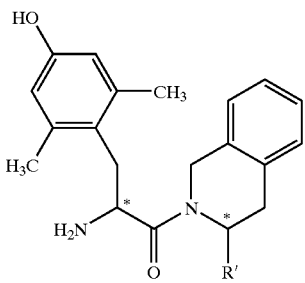

wherein R' is selected from the group consisting of

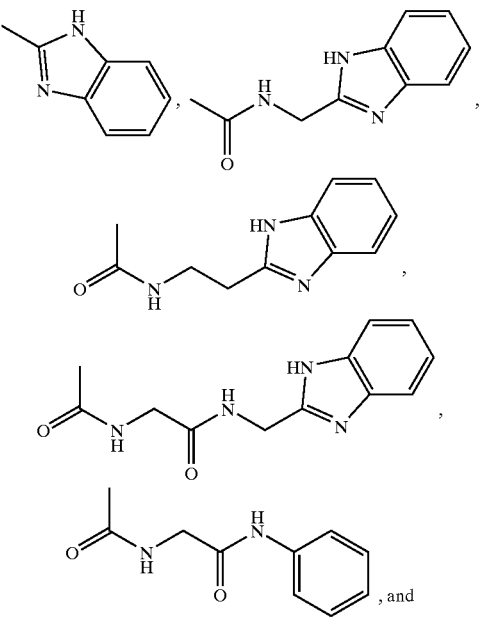, and

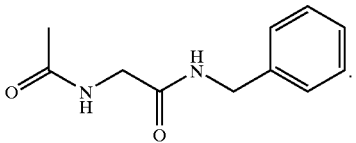.

The present inventive compounds can be synthesized by standard methods known to those of ordinary skill in the art. See, for example, *Modern Techniques of Peptide and Amino Acid Analysis*, John Wiley & Sons (1981); Bodansky, *Principles of Peptide Synthesis*, Springer Verlag (1984)). Specific examples of the synthesis of the present inventive compounds are set forth in the Examples herein.

The spacer "X" comprises one or more amino acid residues, which comprise an amino group and a carbonyl, preferably in the form of an amide group. Preferably, the spacer comprises 1–6 amino acid residues, more preferably 1–3 amino acid residues, even more preferably 1–2 amino acid residues, and most preferably 1 amino acid residue. In some embodiments, "X" does not exist.

Figure 2:
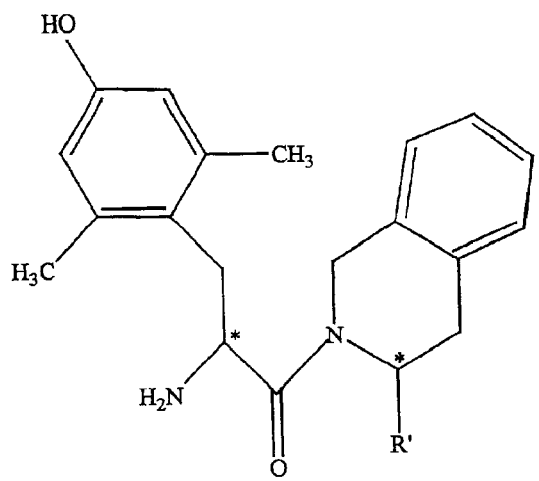
FIG. 2 depicts compounds of the present invention.
Figure 2:
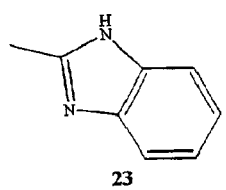
Figure 2:
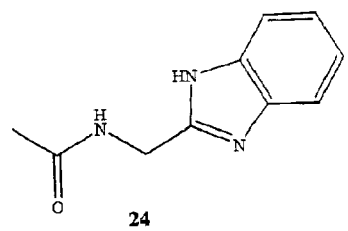
Figure 2:
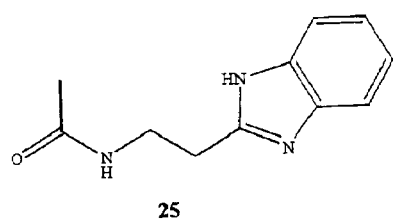
Figure 2:
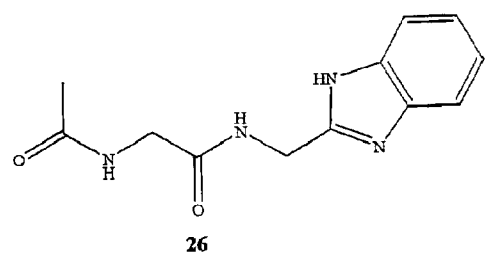
Figure 2:
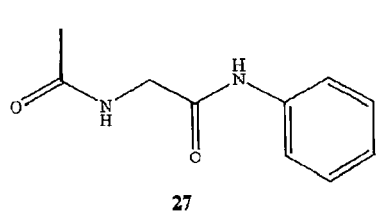
Figure 2:
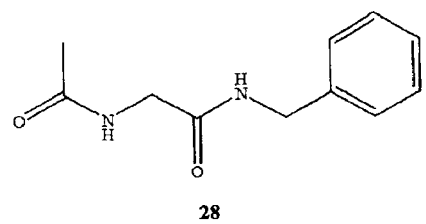

"Y" is desirably an aromatic group, such as, for example phenyl, benzyl, or benzoimidazolyl, which are optionally substituted. The aromatic group "Y" can be substituted with 1 to 3 substituents such as, for example, $C_1$–$C_6$ alkyl, $C_1$–$C_6$ alkenyl, halo, amino, haloalkyl, hydroxy, $C_1$–$C_6$ alkoxy, phenyl or nitro. Preferably, "Y" is phenyl, benzyl, or benzoimidazolyl. FIG. 2 provides examples of suitable spacers "X" and aromatic groups "Y".

Without wishing to be bound to any particular theory, alteration in the C-terminus of the Dmt-Tic pharmacophore appears to mimic changes observed with the amphibian $\mu$ opioid heptapeptides dermorphin and deltorphin (Melchiorri et al., *Gen. Pharmac.*, 27: 1099–1107 (1996); Lazarus et al., *Prog. Neurobiol.*, 57: 377–420 (1999)). Furthermore, a third aromatic nucleus (i.e., "Y") determines δ-opioid agonist activity, when it is located at a prescribed distance from the Dmt-Tic pharmacophore by means of a spacer (i.e., "X"). This in turn implies that the $\mu$ receptor binding site not only accommodates, but also requires, a physically larger and bulkier peptide ligand in order to bind and trigger an agonist response.

Whether an above-described compound functions as an agonist, a partial agonist, an antagonist, a partial antagonist, or a mixed agonist/antagonist is set forth, in part, in the Examples herein. Additionally, conventional techniques known to those of ordinary skill in the art can be used to make such determinations. Examples of such techniques include, but are not limited to, the mouse vas deferens in vitro assay of δ receptors and the guinea pig ileum in vitro assay of $\mu$ receptors as described in the Examples. Examples of in vivo studies include, but are not limited to, the tail flick test (Harris et al., *J. Pharmacol. Meth.* 20: 103–108 (1988); and Sing et al., *P.A. Amber (v. 3.0. rev. A)*, Dept. Pharm. Chem., University of California, San Francisco (1988)).

The present invention further provides a composition comprising at least one of the above compounds. Desirably, the composition comprises at least one carrier, which is preferably a pharmaceutically acceptable carrier, diluent or vehicle. Also, desirably, the composition is formulated for human administration. Pharmaceutically acceptable carriers are well-known to those of ordinary skill in the art, as are suitable methods of administration. The choice of carrier will be determined, in part, by the particular method used to administer the composition. One of ordinary skill in the art will also appreciate that various routes of administering a composition are available, and, although more than one route can be used for administration, a particular route can provide a more immediate and more effective reaction than another route. Accordingly, there are a wide variety of suitable formulations of compositions that can be used in the present inventive methods.

A compound of the present invention can be made into a formulation suitable for parenteral administration, preferably intraperitoneal administration, or dural administration. Such a formulation can include aqueous and nonaqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The formulations can be presented in unit dose or multi-dose sealed containers, such as ampules and vials, and can be stored in a freeze-dried (lyophilized) condition requiring only the addition of the sterile liquid carrier, for example, water, for injections, immediately prior to use. Extemporaneously injectable solutions and suspensions can be prepared from sterile powders, granules, and tablets, as described herein.

A formulation suitable for oral administration can consist of liquid solutions, such as an effective amount of the compound dissolved in diluents, such as water, saline, or fruit juice; capsules, sachets or tablets, each containing a predetermined amount of the active ingredient, as solid or granules; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers.

Similarly, a formulation suitable for oral administration can include lozenge forms, which can comprise the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, gels, and the like containing, in addition to the active ingredient, such carriers as are known in the art.

An aerosol formulation suitable for administration via inhalation also can be made. The aerosol formulation can be placed into a pressurized acceptable propellant, such as dichlorodifluoromethane, propane, nitrogen, and the like.

A formulation suitable for topical application can be in the form of creams, ointments, or lotions.

A formulation for rectal administration can be presented as a suppository with a suitable base comprising, for example, cocoa butter or a salicylate. A formulation suitable for vaginal administration can be presented as a pessary, tampon, cream, gel, paste, foam, or spray formula containing, in addition to the active ingredient, such carriers as are known in the art to be appropriate.

Any of the above compositions can further comprise one or more other active agents. Alternatively, any of the above compositions can be administered, by the same or different route, in combination with another composition comprising one or more other active agents, either simultaneously or sequentially in either order sufficiently close in time to realize the benefit of such co-administration.

In view of the above, the present invention provides a method of treating a mammal in need of an antagonist of a δ-opioid receptor. The method comprises administering at least one compound of formula:

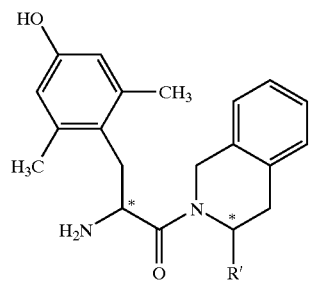

wherein R' is

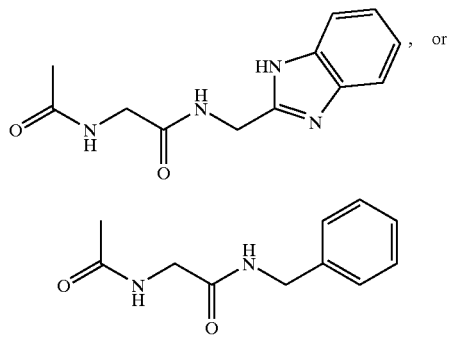

in an amount that antagonizes a δ-opioid receptor in said mammal.

The present invention further provides a method of treating a mammal in need of an agonist of a δ-opioid receptor. The method comprises administering at least one compound of formula:

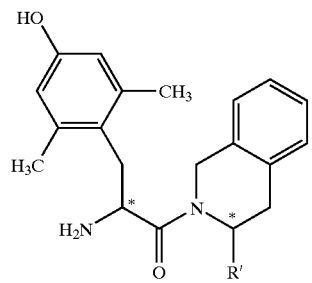

wherein R' is

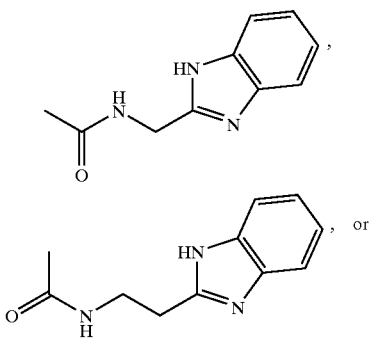

-continued

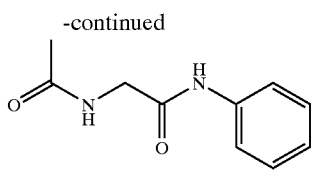

in an amount that agonizes a δ-opioid receptor in said mammal.

In the context of the above method, if the mammal is also in need of an agonist of a μ-opioid receptor, the compound of formula:

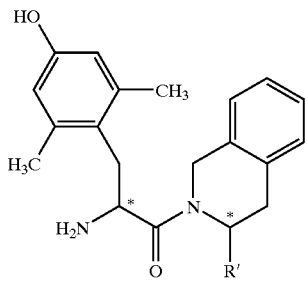

is the compound wherein R' is

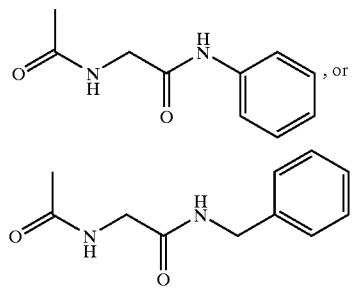, or

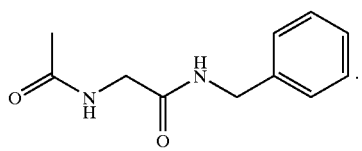.

Such a method and compounds are useful to induce analgesia.

The present invention further provides a method of treating a mammal in need of an antagonist of a δ-opioid receptor and an agonist of a μ-opioid receptor, which method comprises administering the compound of formula:

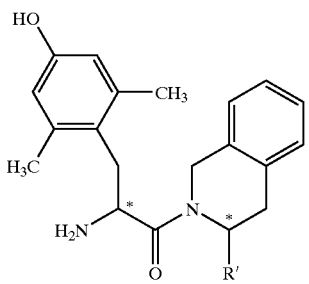

wherein R' is

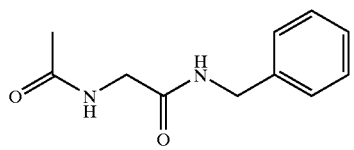

in an amount that antagonizes a δ-opioid receptor and agonizes a μ-opioid receptor in said mammal.

The dose administered to a mammal, particularly a human, in the context of the present invention should be sufficient to effect a therapeutic response in the individual over a reasonable time frame. The dose will be determined by the potency of the particular compound employed for treatment, the severity of any condition to be treated, as well as the body weight and age of the individual. The size of the dose also will be determined by the existence of any adverse side effects that may accompany the use of the particular compound employed. It is always desirable, whenever possible, to keep adverse side effects to a minimum.

The dosage can be in unit dosage form, such as a tablet or capsule. The term "unit dosage form" as used herein refers to physically discrete units suitable as unitary dosages for human and animal subjects, each unit containing a predetermined quantity of a compound, alone or in combination with other active agents, calculated in an amount sufficient to produce the desired effect in association with a pharmaceutically acceptable diluent, carrier, or vehicle. The specifications for the unit dosage forms of the present invention depend on the particular embodiment employed and the effect to be achieved, as well as the pharmacodynamics associated with each compound in the host. The dose administered should be an effective amount, i.e., an amount effective to antagonize or agonize a δ-opioid receptor or a μ-opioid receptor as desired.

Since the "effective amount" is used as the preferred endpoint for dosing, the actual dose and schedule can vary, depending on interindividual differences in pharmacokinetics, drug distribution, and metabolism. The "effective amount" can be defined, for example, as the blood or tissue level desired in the patient that corresponds to a concentration of one or more compounds according to the invention. The "effective amount" for a given compound of the present invention also can vary when the composition of the present invention comprises another active agent or is used in combination with another composition comprising another active agent.

One of ordinary skill in the art can easily determine the appropriate dose, schedule, and method of administration for the exact formulation of the composition being used, in order to achieve the desired "effective amount" in the individual patient. One skilled in the art also can readily determine and use an appropriate indicator of the "effective amount" of the compound of the present invention by pharmacological end-point analysis.

Further, with respect to determining the effective amount in a patient, suitable animal models are available and have been widely implemented for evaluating the in vivo efficacy of such compounds. These models include the tail flick test (see, e.g., U.S. Pat. No. 5,780,589). In vitro models are also available, examples of which are set forth in the Examples herein.

Generally, an amount of a present inventive compound up to about 50 mg/kg body weight, preferably from about 10 mg/kg body weight to about 50 mg/kg body weight is preferred, especially from about 10 mg/kg body weight to about 20 mg/kg body weight. In certain applications, multiple daily doses are preferred. Moreover, the number of doses will vary depending on the means of delivery and the particular compound administered.

EXAMPLES

The following examples serve to illustrate further the present invention and are not intended to limit its scope in any way.

Nomenclature as established by the IUPAC-IUB Commission on Biochemical Nomenclature (*J. Biol. Chem.* 260: 1442 (1985)) will be used herein. In addition, the following symbols and abbreviations will be used:

AD: 1-adamantyl amide
BBB: blood-brain barrier
Boc: tert-butyloxycarbonyl
DAGO: H-Tyr-D-Ala-Gly-N-MePhe-Gly-ol ($\mu$ agonist)
DAMME: H-Tyr-D-Ala-Gly-N-MePhe-Met(O)-ol ($\mu$ agonist)
DCC: N,N'-dicyclohexylcarbodiimide
Deltorphin A: H-Tyr-D-Met-Phe-His-Leu-Met-NH$_2$ ($\delta_1$ agonist)
Deltorphin B: H-Tyr-D-Ala-Phe-Glu-Val-Val-Gly-NH$_2$ ($\delta_2$ agonist)
DER: dermorphin or H-Tyr-D-Ala-Phe-Gly-Tyr-Pro-Ser-NH$_2$ ($\mu$ agonist)
DMF: N,N-dimethylformamide
DMSO: dimethylsulfoxide
Dmt or D: 2',6'-dimethyl-L-tyrosine
DPD: H-Dmt-D-Phe-Gly-Val-Val-NH$_2$ ($\mu$ antagonist)
DPDPE: H-Tyr-[D-Pen-Gly-Phe-D-Pen] enkephalin ($\delta_1$ agonist)
DSB: H-Dmt-Sar-Bid ($\delta/\mu$ agonist)
DTA: H-Dmt-Tic-Ala-NH$_2$ ($\delta$ antagonist)
DtMe: H-Dmt-Tic-NHCH$_3$ ($\delta$ antagonist)
Et: ethyl
Et$_2$O: diethyl ether
EtPt: petroleum ether
GPI: guinea pig ileum ($\mu$ receptor bioassay)
H-$\alpha$Dmt-OH: 2-methylamino-3-(2',6'-dimethyl-4-hydroxyphenyl)-propionic acid
H-$\beta$Tic-OH: 1,2,3,4-tetrahydroisoquinoline-3-yl acetic acid
hMDR-1: human multidrug resistance glycoprotein (Pgp)-1
HOBt: 1-hydroxybenzotriazole
HPLC: high performance liquid chromatography
K$_e$: the antilog of pA$_2$ in molar concentration
LiAlH$_4$: lithium aluminum hydride
Me: methyl
MeDTOH: N,N(Me)$_2$-Dmt-Tic-OH ($\delta$ antagonist)
MeOH: methanol
MVD: mouse vas deferens ($\delta$ specific bioassay)
NaBH$_3$CN: sodium cyanoborohydride
NAL: naltrindole
NH-tBut: tert-butyl amine
NMM: N-methyl morpholine
OMe: methyl ester
PA$_2$: negative log of the molar concentration required to double the agonist concentration to achieve the original response
PipDTOH: [des-NH$_2$-$\alpha$-piperidine-1-yl]Dmt-Tic-OH ($\delta$ antagonist)
tBu: tert-butyl
TEA: triethylamine
TFA: trifluoroacetic acid
Tic or T: 1,2,3,4-tetrahydroisoquinoline-3-carboxylic acid
TIP(P): H-Tyr-Tic-Phe-(Phe)-OH
TLC: thin layer chromatography
[Trp$^4$,Tyr$^5$]DER: H-Tyr-D-Ala-Phe-Trp-Tyr-NH$_2$ ($\mu$ agonist)
[Trp$^4$,Lys-OH$^7$]DER: H-Tyr-D-Ala-Phe-Trp-Tyr-Pro-Lys-OH ($\mu$ agonist)
WSC: 1-ethyl-3-[3'-dimethyl-aminopropyl]carbodiimide hydrochloride
Z: benzyloxycarbonyl Verapamil, colchicine and sodium pyruvate were obtained from Sigma Chemical Co. (St. Louis, Mo.). DPDPE and DAGO were obtained from Bachem (Torrance, Calif.). Boc-Tic-OH was obtained from Bachem Feinchemikalien AG (Bubendorf, Switzerland). Naloxone, naltrindole and BNTX were obtained from Research Biochemicals International (Natick, Mass.). Vybrant MDR assay is a product of Molecular Probes (Eugene, Oreg.). [$^3$H]DPDPE was from NEN-DuPont (Billerica, Mass.) and [$^3$H]DAGO (60 Ci/mmol) was from Amersham (Arlington Heights, Ill.).

H-L-Dmt-OH was synthesized as previously described (Dygos et al., *Synthesis* 8: 741–743 (1992)). Boc-Tic-OH was obtained from Bachem (Heidelberg, Germany). All peptides were prepared by standard solution methods (Lazarus et al., *Biochem. Biophys. Res. Commun.* 178: 110–115 (1991); Sagan et al., *Biochem. Biophys. Res. Commun.* 187: 1203–1210 (1992)). Dipeptides were obtained by condensation of Boc-L-Dmt-OH with Tic derivatives (H-Tic-OtBu, H-Tic-NHMe, H-Tic-NH-1-adamantane and H-$\beta$Tic-OMe) or by condensation of Boc-Dmt-Tic-OH with tert-butyl amine or 5-aminotetrazolyl via DCC/HOBt. Tripeptides were obtained by condensation of Boc-L-Dmt-Tic-OH with Ala derivatives (H-Ala-NHMe, H-Ala-NH-1-adamantane, H-Ala-NH-tBu and H-Ala-OMe) via DCC/HOBt. Final products were obtained, when necessary, by ester function hydrolysis with 1 N NaOH and removal of the Boc protecting group in TFA. N-alkylated di- and tripeptide derivatives were obtained by reductive alkylation of the corresponding deprotected linear peptides with aldehydes (formaldehyde, glutaraldehyde, succinaldehyde) and NaBH$_3$CN in acetonitrile (Borch et al., *J. Org. Chem.* 37: 1673–1674 (1972)). HCl.H-$\beta$H-Tic-OMe was prepared by reduction of H-Tic-OMe with LiAlH$_4$ to the corresponding 3-hydroxymethyl-Tic that was transformed first in 3-bromomethyl-Tic and then in 3-cyano-Tic. Treatment of the cyano group with HCl-methanol gave the final product (Crabb et al., *J. Chem. Soc. Perkins Trans. II:* 370–378 (1977)). $\alpha$-H(R,S)-Dmt-Tic-OH was obtained by condensation of (R,S)-2-cyano-3-(4-hydroxy-2,6-dimethylphenyl)-propanoic acid with H-Tic-OtBu via DCC/HOBt. In turn, (R,S)-2-cyano-3-(4-hydroxy-2,6-dimethylphenyl)-propanoic acid was prepared from ethyl cyanoacetate and O-carbethoxy-3,5-dimethyl-4-chloromethylphenol (Abrash et al., *Biochemistry* 2: 947–952 (1972)).

Preparative reversed-phase HPLC was conducted with either a Waters Delta Prep 3000 Å (30×3 cm; 15 $\mu$m) column or a Waters Delta Prep 4000 system with Waters Prep LC 40 mm Assembly column $C_{18}$ (30×4 cm, 300 A, 15 μm particle size column). Peptides were eluted with a gradient of either 0–60% or 0–50% B in 25 min at a flow rate of 50 ml/min using the following mobile phases: solvent A (10% acetonitrile in 0.1% TFA, v/v) and solvent B(60% acetonitrile in 0.1% TFA, v/v). Analytical HPLC analyses were carried out with a Bruker Liquid Chromatographer LC21-C instrument using a Vydac 218 TP 5415 C18 column (250×4.6 mm, 5 μm particle size) and equipped with a Bruker LC 313 UV variable wavelength detector. Recording and quantification were accomplished with a chromatographic data processor coupled to an Epson computer system (QX-10). Analytical determinations and capacity factor (K') of the products were determined using HPLC conditions in the above solvent systems (solvents A and B) programmed at a flow rate of 1 ml/min using the following linear gradients: (a) from 0 to 100% B in 25 min, and (b) from 10 to 70% B in 25 min. All analogues showed less than 1% impurities when monitored at 220 and 254 nm.

TLC was performed on precoated plates of silica gel F254 (Merck, Darmstadt, Germany) using the following solvent systems: (a) 1-butanol/AcOH/$H_2O$ (3:1:1, v/v/v) and (B) $CH_2Cl_2$/toluene/methanol (17:1:2, v/v/v). Ninhydrin (1%, Merck), fluorescamine (Hoffman-LaRoche), and chlorine reagents were used as sprays. Open column chromatography (2×70 cm, 0.7–1 g material) was used on silica gel 60 (70–230 mesh, Merck) using the same eluent systems.

Melting points were determined on a Kofler apparatus and are uncorrected. Optical rotations were determined at 10 mg/ml in methanol with a Perkin-Elmer 241 polarimeter with a 10 cm water-jacketed cell. All $^1$H-NMR spectra were recorded on a Bruker 200 MHZ spectrometer. Matrix-assisted laser desorption ionization time of flight (MALDI-TOF) mass spectrometry analyses of peptides were conducted using a Hewlett Packard G 2025 A LD-TOF system. The samples were analyzed in the linear mode with 28 kV accelerating voltage, mixing them with a saturated solution of α-cyano-4-hydroycinnamic acid matrix.

Example 1

This example describes the synthesis of Boc-Dmt-Tic-OMe.

HOBt (0.22 g, 1.42 mmol) and DCC (0.29 g, 1.42 mmol) were added to a solution of Boc-Dmt-OH (0.4 g, 1.29 mmol) and H-Tic-OMe (0.25 g, 1.29 mmol, Hayashi et al., *Chem. Pharm. Bull.* 31: 312–314 (1983)). The reaction was stirred for 3 hr at 0° C. and for 24 hr at room temperature (RT). After evaporation of DMF, the residue was solubilized in EtOAc and washed with citric acid (10%), $NaHCO_3$ (5%) and brine. The organic phase was dried and evaporated to dryness. The residue was crystallized from $Et_2O$/PtEt (1:1, v/v): yield 0.52 g (83%); $R_f$(B) 0.81;HPLC K'=7.91; mp 135–137° C.; $[α]^{20}D$-13.2; $MH^+$ 483; $^1$H-NMR (DMSO) δ=1.37–1.46 (d, 9H), 2.16 (s, 6H), 2.96–3.01 (m, 2H), 3.08–3.13 (m, 2H), 3.46–3.56 (m, 1H), 3.72 (s, 3H), 4.34–4.88 (m, 3H), 6.46 (s, 2H), 7.18–7.21 (m, 4H), 8.32 (bs, 1H).

Example 2

This example describes the synthesis of Boc-Dmt-Tic-$NHNH_2$.

$NH_2NH_2·H_2O$ (1 ml) was added to a solution of Boc-Dmt-Tic-OMe (0.26 g, 0.54 mmol) in MeOH (10 ml). The reaction mixture was stirred for 24 hr at RT. After evaporation of the solvent, the residue was crystallized from $Et_2O$/PtEt (1:1, v/v): yield 0.25 g (94%); $R_f$(B) 0.75; HPLC K'=6.83; mp 154–156° C.; $[α]^{20}D$-14.5; $MH^+$ 483; $^1$H-NMR (DMSO) δ=1.35–1.44 (d, 9H), 2.16 (s, 6H), 3.07–3.40 (s, 4H), 3.79 (m, 1H), 4.29–4.78 (m, 5H), 6.34 (m, 2H), 6.95 (bs, 1H), 7.14 (3, 4H), 8.22 (bs, 1H).

Example 3

This example describes the synthesis of TFA-H-Dmt-Tic-$NHNH_2$ (compound 6 in Table II).

Boc-Dmt-Tic-$NHNH_2$ (0.2 g, 0.41 mmol) was treated with TFA (1 ml) for 0.5 hr at RT. $ET_2O$/PtEt (1:1, v/v) was added to the solution until the product precipitated: yield 0.18 g (91%); $R_f$(A) 0.69; HPLC K'=2.52; mp 143–145° C.; $[α]^{20}D$+13.5; $MH^+$ 382. Anal. ($C_{12}H_{26}N_4O_3$·TFA) C,H,N (C 65.95, H 6.88, N 14.65).

Example 4

This example describes the synthesis of Z-Tic-NHMe.

NMM (0.35 ml, 3.21 mmol), HOBt (0.54 g, 3.53 mmol) and DCC (0.73 g, 3.53 mmol) were added to a solution of Z-Tic-OH (1 g, 3.21 mmol, Abrash (1972), supra) and HCl.$H_2$NMe (0.22 g, 3.21 mmol) in DMF (10 ml) at 0° C. The reaction mixture was stirred for 3 hr at 0° C. and 24 hr at RT. After evaporation of DMF, the residue was solubilized in EtOAc and washed with citric acid (10%), $NaHCO_3$ (5%) and brine. The organic phase was dried and evaporated to dryness. The residue was crystallized from $Et_2O$/PtEt (1:1, v/v): yield 0.90 g (87%); $R_f$(B) 0.97;HPLC K'=8.56; mp 137–139° C.; $[α]^{20}D$+ 13.5; $MH^+$ 325; $^1$H-NMR (DMSO) δ=2.44 –2.46 (d, 3H), 3.12–3.24 (m, 2H), 4.36–4.46 (m, 3H), 5.17 (s, 2H), 7.18–7.21 (m, 5H), 7.36–7.39 (m, 4H), 7.74–7.77 (m, 1H).

Example 5

This example describes the synthesis of H-Tic-NHMe.

C/Pd (5%, 0.05 g) was added to a solution of Z-Tic-NHMe (0.90 g, 2.78 mmol) in MeOH (30 ml) and $H_2$ was bubbled for 1 hr at RT. After filtration, the solution was evaporated to dryness. The residue was crystallized from $Et_2O$/PtEt (1:1, v/v): yield 0.49 g (92%); $R_f$(B) 0.38; HPLC K'=5.03; mp 123–125° C.; $[α]^{20}D$+18.7; $MH^+$ 191.

Example 6

This example describes the synthesis of Boc-Dmt-Tic-NHMe.

Boc-Dmt-OH was condensed with H-Tic-NHMe via DCC/HOBt as described in Example 1 in order to obtain Boc-Dmt-Tic-NHMe: yield 0.13 g (85%); $R_f$(B) 0.73; HPLC K'=6.34; mp 142–146° C.; $[α]^{20}D$-15.3; $MH^+$ 482; $^1$H-NMR (DMSO)δ=1.35–1.44 (d, 9H), 2.16 (s, 6H), 2.44–2.46 (d, 3H), 3.05–3.41 (m, 4H), 3.79 (m, 1H), 4.29–4.78 (m, 3H), 6.34 (s, 2H), 6.95 (bs, 1H), 7.14 (s, 4H), 8.22 (bs, 1H).

Example 7

This example describes the synthesis of TFA·H-Dmt-Tic-NHMe (compound 7 in Table II).

Boc-Dmt-Tic-NHMe was treated with TFA as reported in Example 3: yield 0.12 g (93%); $R_f$(A) 0.69; HPLC K'=3.10; mp 152–154° C.; $[α]^{20}D$=22.0; $MH^+$ 382. Anal. ($C_{22}H_{27}N_3O_3$·TFA) C, H, N (C 69.27, H 7.13, N 11.02).

Example 8

This example describes the synthesis of TFA-N,N-(Me)$_2$-Dmt-Tic-NHMe (compound 13 in Table II).

This compound was obtained by exhaustive methylation of TFA·H-Dmt-Tic-NHMe as described in Example 30: yield 0.12 g (96%); R$_f$(A) 0.71; HPLC K'=3.19; mp 156–158° C.; [α]$^{20}$D–19.3; MH$^+$ 410. Anal. (C$_{24}$H$_{31}$N$_3$O$_3$·TFA) C, H, N (C 70.39, H 7.63, N 10.26).

Example 9

This example describes the synthesis of TFA·H-Dmt-Tic-OMe (compound 8 in Table II).

Boc-Dmt-Tic-OMe was treated with TFA as described in Example 3: yield 0.25 g (92%); R$_f$(A) 0.81;HPLC K'=3.83; mp 118–120° C.; [α]$^{20}$D–24.0; MH$^+$ 382. Anal. (C$_{22}$H$_{26}$N$_2$O$_4$·TFA) C, H, N (C 69.09, H 6.85, N 7.32).

Example 10

This example describes the synthesis of Boc-Dmt-βHTic-OMe.

This compound was obtained by condensation of Boc-Dmt-OH with HCl.βHTic-OMe (Crabb et al., *J. Chem. Soc. Perkins Trans. II:* 370–378 (1977)) [R$_f$(B) 0.38, HPLC K'=2.31, mp 153–155° C., [α]$^{20}$D–37.5; MH$^+$ 206] via DCC/HOBt as reported for Boc-Dmt-Tic-OMe: yield 0.42 g (97%); R$_f$(B) 0.93; HPLC K'=9.27; mp 94–96° C; [α]$^{20}$D+33.9; MH$^+$ 497; $^1$H-NMR (DMSO) δ=1.82 (s, 9H), 2.35 (s, 6H), 2.80–3.50 (m, 6H), 3.70 (s, 3H), 3.90 (m, 1H), 4.30 (m, 2H), 4.40 (dd, 1H), 6.43 (s, 2H), 7.20 (m, 6H), 9.50 (bs, 1H).

Example 11

This example describes the synthesis of Boc-Dmt-βHTic-OH.

Sodium hydroxide (1N, 1.34 ml) was added to a solution of Boc-Dmt-βTic-OMe (0.42 g, 0.90 mmol) in MeOH (10 ml). The reaction mixture was stirred for 24 hr at RT. After evaporation of the solvent, the residue was solubilized in EtOAc and washed with citric acid (10%) and brine. The organic phase was dried and evaporated to dryness. The residue was crystallized from Et$_2$O: yield 0.42 g (98%); R$_f$(B) 0.35; HPLC K'=7.54; mp 117–119° C.; [α]$^{20}$D+36.2; MH$^+$ 483.

Example 12

This example describes the synthesis of TFA·H-Dmt-βHTic-OH (compound 1 in Table II).

Boc-Dmt-βHTic-OH was treated with TFA as described in Example 3: yield (0.26 g (68%); R$_f$(A) 0.82; HPLC K'=4.9; mp 118–120° C.; [α]$^{20}$D+95.0; MH$^+$ 383; $^1$H-NMR (DMSO) δ=2.2 (s, 6H), 2.80–3.0 (m, 4H), 3.4 (s, 2H), 4.1 (m, 1H), 4.3 (m, 2H), 4.5 (m, 1H), 6.43 (s, 2H), 7.20 (m, 4H), 9.2 (bs, 3H). (C$_{22}$H$_{26}$N$_2$O$_4$·TFA) C, H, N (C 69.09, H 6.85, N 7.32).

Example 13

This example describes the synthesis of Boc-Dmt-Tic-OH.

Sodium hydroxide (1 N, 1.3 ml) was added to a solution of Boc-Dmt-Tic-OMe (0.52 g, 1.08 mmol) in MeOH (10 ml). The reaction mixture was stirred for 24 hr at RT and treated as described in Example 11: yield 0.45 g (89%); R$_f$(B) 0.36; HPLC K'=6.71; mp 147–149° C.; [α]20D–15.6; MH$^+$ 469.

Example 14

This example describes the synthesis of Boc-Dmt-Tic-NH-tetrazole-5-yl.

HOBt (0.14 g, 0.94 mmol) and DCC (0.19 g, 0.94 mmol) were added to a solution of Boc-Dmt-Tic-OH (0.4 g, 0.85 mmol) and 5 aminotetrazole monohydrate (0.1 g, 0.85 mmol) in DMF (10 ml) at 0° C. The reaction mixture was stirred for 3 hr at 0° C. and 24 hr at RT. After evaporation of the DMF, it was treated as described in Example 11; however, the residue was crystallized from Et$_2$O/PtEt (1:1, v/v): yield 0.19 g (42%); R$_f$(B) 0.75;HPLC K'=7.18; mp 146–148° C.; [α]$^{20}$D–23.1; MH$^+$ 537; $^1$H-NMR (DMSO) δ=1.36–1.45 (d, 9H), 2.16 (s, 6H), 2.96–3.0 (m, 2H), 3.08–3.13 (m, 2H), 3.46–3.56 (m, 1H), 4.34–4.88 (m, 3H), 6.46 (s, 2H), 7.18–7.21 (m, 4H), 8.32 (bs, 1H), 8.45 (bs, 1H), 14.39 (bs, 1H).

Example 15

This example describes the synthesis of TFA·H-Dmt-Tic-NH-tetrazole-5-yl (compound 10 in Table II).

Boc-Dmt-Tic-NH-tetrazole-5-yl was treated with TFA as described in Example 3: yield 0.17 g (87%); R$_f$(A) 0.79; HPLC K'3.75; mp 131–133° C.; [α]$^{20}$D–18.3; MH$^+$ 436; $^1$H-NMR (DMSO) δ=2.18 (s, 6H), 2.81–3.03 (m, 2H), 3.12–3.18 (m, 2H), 3.66–3.76 (m, 1H), 4.38–4.52 (m, 3H), 6.45 (s, 2H), 7.21–7.25 (m, 4H), 8.27 (bs, 3H), 8.9 (bs, 3H), 14.39 (bs, 1H). Anal. (C$_{22}$H$_{25}$N$_7$O$_3$·TFA) C, H, N (C 69.68, H 5.79, N22.51).

Example 16

This example describes the synthesis of Boc-Dmt-Tic-Ala-OMe.

NMM (0.05 ml, 0.42 mmol), HOBt (0.07 g, 0.46 mmol) and DCC (0.09 g, 0.46 mmol) were added to a solution of Boc-Dmt-Tic-OH (0.2 g, 0.42 mmol) and HCl.H-Ala-OMe (0.06 g, 0.42 mmol) in DMF (10 ml) at 0° C. the reaction was stirred for 3 hr at 0° C. and 24 hr at RT. After evaporation of DMF, the residue was treated as described in Example 14: yield 0.2 g (85%); R$_f$(B) 0.77; HPLC K'=7.68; mp 124–126° C.; [α]$^{20}$D+40.1; MH$^+$ 555; $^1$H-NMR (DMSO) δ=1.37–1.46 (m, 12H), 2.16 (s, 6H), 2.96–3.01 (m, 2H), 3.08–3.13 (m, 2H), 3.46–3.56 (m, 1H), 3.73 (s, 3H), 4.03–4.07 (q, 1H), 4.34–4.88 (m, 3H), 6.46 (s, 2H), 7.18–7.21 (m, 4H), 8.32 (bs, 1H), 8.51 (bs, 1H).

Example 17

This example describes the synthesis of TFA.H-Dmt-Tic-Ala-OMe (compound 19 in Table II). Boc-Dmt-Tic-Ala-OMe was treated with TFA as described in Example 3: yield 0.19 g (92%); R$_f$(A) 0.64; HPLC K'=3.72; mp 130–132° C.; [α]$^{20}$D+90.1; MH$^+$ 454. Anal. (C$_{25}$H$_{31}$N$_3$O$_3$·TFA) C, H, N (C 66.21,H 6.89, N 9.26).

Example 18

This example describes the synthesis of Boc-Tic-NH-1-adamantane.

NMM (0.20 ml, 1.8 mmol), HOBt (0.30 g, 1.98 mmol) and DCC (0.41 g, 1.98 mmol) were added to a solution of Boc-Tic-OH (0.5 g, 1.8 mmol) and 1-aminoadamantane hydrochloride (0.34 g, 1.8 mmol) in DMF (10 ml) at 0° C. The reaction was stirred for 3 hr at 0° C. and 24 hr at RT. After evaporation of DMF, the residue was treated as described in Example 14: yield 0.6 g (81%); R$_f$(B) 0.89; HPLC K'=9.68; mp 127–129° C.; [α]$^{20}$D+15.3; MH$^+$ 412;

¹H-NMR (DMSO) δ=1.39–1.46 (d, 9H), 1.65 (s, 6H), 1.93–2.07 (m, 9H), 3.08–3.13 (m, 2H), 4.34–4.88 (m, 3H), 7.17–7.20 (m, 4H), 8.08 (bs, 1H).

Example 19

This example describes the synthesis of TFA.H-Tic-NH-1-adamantane.

Boc-Tic-NH-1-adamantane (0.6 g; 1.46 mmol) was treated with TFA (2 ml) for 0.5 hr at RT. Et$_2$O/EtPt (1:1, v/v) was added to the solution until the product precipitated: yield 0.57 g (92%); R$_f$(A) 0.73; HPLC K'=5.80; mp 157–159° C.; [α]$^{20}$D+18.4; MH$^+$ 311.

Example 20

This example describes the synthesis of Boc-Dmt-Tic-NH-1-adamantane.

This compound was obtained by condensation of Boc-Dmt-OH with TFA-H-Tic-NH-1-adamantane via DCC/HOBt as described in Example 1: yield 0.16 g (85%); R$_f$(B) 0.93; HPLC K'=9.28; mp 142–144° C.; [α]$^{20}$D+28.1; MH$^+$ 603; ¹H-NMR (DMSO) δ=1.38–1.45 (d, 9H), 1.64 (s, 6H), 1.93–2.08 (m, 9H), 2.17 (s, 6H), 2.96–3.01 (m, 2H), 3.08–3.13 (m, 2H), 3.47–3.54 (m, 1H), 4.34–4.88 (m, 3H), 6.46 (s, 2H), 7.17–7.20 (m, 4H), 8.27 (bs, 1H), 8.47 (bs, 1H).

Example 21

This example describes the synthesis of TFA·H-Dmt-Tic-NH-1-adamantane (compound 11 in Table II).

Boc-Dmt-Tic-NH-1-adamantane was treated with TFA as described in Example 3: yield 0.15 g (94%; R$_f$(A) 0.64; HPLC K'=6.98; mp 180–182° C.; [α]$^{20}$D−2.7; MH$^+$ 502. Anal. (C$_{31}$H$_{39}$N$_3$O$_3$·TFA) C, H, N (C 74.22, H 7.84, N 8.38).

Example 22

This example describes the synthesis of Boc-D-Tic-NH-1-adamantane.

This compound was obtained by condensation of Boc-D-Tic-OH with 1-amino adamantane hydrochloride as described in Example 18: yield 0.6 g (81%); R$_f$(B) 0.89; HPLC K'=9.68; mp 127–129° C.; [α]$^{20}$D−15.3; MH$^+$ 412; ¹H-NMR (DMSO) δ=1.39–1.46 (d, 9H), 1.65 (s, 6H), 1.93–2.07 (m, 9H), 3.08–3.13 (m, 2H), 4.34–4.88 (m, 3H), 7.17–7.20 (m, 4H), 8.08 (bs, 1H).

Example 23

This example describes the synthesis of TFA·H-D-Tic-NH-1-adamantane.

Boc-D-Tic-NH-1-adamantane was treated with TFA as reported for TFA.H-Tic-NH-1-adamantane: yield 0.57 g (92%); R$_f$(A) 0.73; HPLC K'=5.80; mp 157–159° C.; [α]$^{20}$D−18.4; MH$^+$ 311.

Example 24

This example describes the synthesis of Boc-Dmt-D-Tic-NH-1-adamantane.

This compound was obtained by condensation of Boc-Dmt-OH with TFA-H-D-Tic-NH-1-adamantane via DCC/HOBt as described in Example 1: yield 0.16 g (85%); R$_f$(B) 0.87; HPLC K'=9.54; mp 135–137° C.; [α]$^{20}$D+14.2; MH$^+$ 603; ¹H-NMR (DMSO) δ=1.39–1.46 (d, 9H), 1.63 (s, 6H), 1.94–2.09 (m, 9H), 2.16 (s, 6H), 2.97–3.03 (m, 2H), 3.05–3.14 (m, 2H), 3.49–3.56 (m, 1H), 4.41–4.91 (m, 3H), 6.41 (s, 2H), 7.18–7.20 (m, 4H), 8.31 (bs, 1H), 8.43 (bs, 1H).

Example 25

This example describes the synthesis of TFA·H-Dmt-D-Tic-NH-1-adamantane (compound 12 in Table II).

Boc-Dmt-D-Tic-NH-1-adamantane was treated with TFA as described in Example 3: yield 0.15 g (94%); R$_f$(A) 0.58; HPLC K'=7.24; mp 164–166° C.; [α]$^{20}$D+27.5; MH$^+$ 502. Anal. (C$_{31}$H$_{39}$N$_3$O$_3$·TFA) C, H, N (C 74.22, H 7.84, N 8.38).

Example 26

This example describes the synthesis of Boc-Ala-NH-1-adamantane.

NMM (0.20 ml, 1.8 mmol), HOBt (0.30 g, 1.98 mmol) and DCC (0.41 g, 1.98 mmol) were added to a solution of Boc-Ala-OH (0.34 g, 1.8 mmol) and 1-amino adamantane hydrochloride (0.34 g, 1.8 mmol) in DMF (10 ml) at 0° C. The reaction was stirred for 3 hr at 0° C. and 24 hr at RT. After evaporation of DMF, the residue was treated as described in Example 14: yield 0.52 g (89%); R$_f$(B) 0.85; HPLC K'=7.73; mp 107–109° C.; [α]$^{20}$D+5.9; MH$^+$ 324; ¹H-NMR (DMSO) δ=1.38–1.45 (m, 12H), 1.65 (s, 6H), 1.93–2.07 (m, 9H), 4.04–4.07 (q, 1H), 8.08 (bs, 1H), 8.42 (bs, 1H).

Example 27

This example describes the synthesis of TFA·H-Ala-NH-1-adamantane.

Boc-Ala-NH-1-adamantane (0.52 g, 1.6 mmol) was treated with TFA (2 ml) for 0.5 hr at RT. Et$_2$O/EtPt (1:1, v/v) was added to the solution until the product precipitated: yield 0.5 g (92%); R$_f$(A) 0.82; HPLC K'=4.95; mp 131–133° C.; [α]$^{20}$D+6.8; MH$^+$ 224.

Example 28

This example describes the synthesis of Boc-Dmt-Tic-Ala-NH-1-adamantane.

This compound was obtained by condensation of Boc-Dmt-Tic-OH with TFA.H-Ala-NH-1-adamantane via DCC/HOBt as described in Example 16: yield 0.12 g (87%); R$_f$(B) 0.91; HPLC K'=9.32; mp 137–139° C.; [α]$^{20}$D+15.5; MH$^+$ 674; ¹H-NMR (DMSO) δ=1.38–1.45 (d, 12H), 1.64 (s, 6H), 1.93–2.08 (m, 9H), 2.17 (s, 6H), 2.96–3.01 (m, 2H), 3.08–3.13 (m, 2H), 3.47–3.54 (m, 1H), 4.03–4.07 (m, 1H), 4.34–4.88 (m, 3H), 6.46 (s, 2H), 7.17–7.20 (m, 4H), 8.27 (bs, 1H), 8.47 (bs, 1H), 8.53 (bs, 1H).

Example 29

This example describes the synthesis of TFA·H-Dmt-Tic-Ala-NH-1-adamantane (compound 21 in Table II).

Boc-Dmt-Tic-Ala-NH-1-adamantane was treated with TFA as described in Example 3: yield 0.11 g (92%); R$_f$(A) 0.65; HPLC K'=6.91; mp 163–165° C.; [α]$^{20}$D+20.1; MH$^+$ 574. Anal. (C$_{34}$H$_{44}$N$_4$·TFA) C, H, N (C 71.3, H 7.74, N 9.78).

Example 30

This example describes the synthesis of TFA·N,N-(Me)$_2$-Dmt-Tic-NH-1-adamantane (compound 15 in Table II).

NMM (0.01 ml, 0.11 mmol), 37% aqueous formaldehyde (0.07 ml, 0.83 mmol) and sodium cyanoborohydride (0.016 g, 0.25 mmol) were added to a stirred solution of TFA·H-Dmt-Tic-NH-1-adamantane (0.7 g, 0.11 mmol) in acetonitrile (10 ml). Glacial acetic acid (0.02 ml) was added over 10 min and the reaction was stirred at RT for 2 hr. The reaction mixture was evaporated in vacuo to give a crude product that was purified by preparative HPLC: yield 0.06 g (90%); $R_f(A)$ 0.64; HPLC K'=7.44; mp 118–120° C.; $[\alpha]^{20}D$−58.01; MH$^+$ 530. Anal. ($C_{33}H_{43}N_3O_3$·TFA) C, H, N (C 74.82, H 8.18, N 7.93).

Example 31

This example describes the synthesis of TFA·N,N-(Me)$_2$-Dmt-D-Tic-Ala-NH-1-adamantane (compound 16 in Table II).

This compound was obtained by exhaustive methylation of TFA·H-Dmt-D-Tic-NH-1-adamantane as described in Example 30: yield 0.06 g (90%); $R_f(A)$ 0.61; HPLC K'=7.53; mp 134–136° C.; $[\alpha]^{20}D$+8.2; MH$^+$ 530. Anal. ($C_{33}H_{43}N_3O_3$·TFA) C, H, N (C 74.82, H 8.18, N 7.93).

Example 32

This example describes the synthesis of Boc-Dmt-Tic-Ala-NHMe.

This compound was obtained by condensation of Boc-Dmt-Tic-OH with HCl·H-Ala-NHMe via DCC/HOBt as described in Example 16: yield 0.25 g (84%); $R_f(B)$ 0.78; HPLC K'=8.90; mp 131–133° C.; $[\alpha]^{20}D$+42.7; MH$^+$ 553; $^1$H-NMR (DMSO) δ=1.37–1.46 (m, 12H), 2.16 (s, 6H), 2.44–2.46 (d, 3H), 2.96–3.01 (m, 2H), 3.08–3.13 (m, 2H), 3.46–3.56 (m, 1H), 4.03–4.07 (q, 1H), 4.34–4.88 (m, 3H), 6.46 (s, 2H), 7.18–7.35 (m, 4H), 8.32 (bs, 1H), 8.43 (bs, 1H), 8.51 (bs, 1H).

Example 33

This example describes the synthesis of TFA·Dmt-Tic-Ala-NHMe (compound 18 in Table II).

Boc-Dmt-Tic-Ala-NHMe was treated with TFA as described in Example 3: yield 0.24 g (91%); $R_f(A)$ 0.58; HPLC K'=4.29; mp 142–144° C.; $[\alpha]^{20}D$+28.5; MH$^+$ 453. Anal. ($C_{25}H_{32}N_4O_4$·TFA) C, H, N (C 66.35, H 7.13, N 12.38).

Example 34

This example describes the synthesis of TFA·[des-NH$_2$-α-piperidine-1-yl-Dmt]-Tic-OH (compound 3 in Table II).

NMM (0.07 ml, 0.62 mmol), 50% aqueous glutaraldehyde (0.38 ml, 2.36 mmol) and sodium cyanoborohydride (0.45 g, 0.73 mmol) were added to a stirred solution of TFA·H-Dmt-Tic-OH (0.15 g, 0.31 mmol, Matthes et al., *Nature* 383: 819–823 (1996)) in acetonitrile (10 ml). Glacial acetic acid (0.06 ml) was added over 10 min and the reaction was stirred at RT for 2 hr. The reaction mixture was evaporated in vacuo to give a crude product that was purified by preparative HPLC: yield 0.16 g (90%); $R_f(A)$ 0.74; HPLC K'=3.66; mp 205–207° C.; $[\alpha]^{20}D$−14.2; MH$^+$ 437. Anal. ($C_{26}H_{32}N_2O_4$·TFA) C, H, N (C 71.53, H 7.39, N 6.42).

Example 35

This example describes the synthesis of TFA·[des-NH$_2$-α-pyrrolidine-1-yl-Dmt]-Tic-OH (compound 4 in Table II) and TFA·[des-NH$_2$-α-pyrrole-1-yl-Dmt]-Tic-OH (compound 5 in Table II).

These two compounds were obtained by reductive alkylation of TFA·H-Dmt-Tic-OH with succinaldehyde as described in Example 34. Analytical data for compound 4: yield 0.016 g (20%); $R_f(A)$ 0.81; HPLC K'=2.68; mp 168–170° C.; $[\alpha]^{20}D$+45.2; MH$^+$ 423. Anal. ($C_{25}H_{30}N_2O_4$·TFA) C, H, N (C 71.07, H 7.16, N 6.63).

Analytical data for compound 5: yield 0.1 g (80%); $R_f(A)$ 0.67; HPLC K'=5.85; mp 185–187° C.; $[\alpha]^{20}D$−56.4; MH$^+$ 421. Anal. ($C_{25}H_{26}N_2O_4$·TFA) C, H, N (C 71.75, H 6.26, N 6.29).

Example 36

This example describes the synthesis of Boc-Dmt-Tic-NH-tBu.

This intermediate was obtained by condensation of Boc-Dmt-Tic-OH with tert-butyl amine via DCC/NMM as described in Example 14: yield 0.26 g (87%); $R_f(B)$ 0.88; HPLC K'=7.02; mp 153–155° C.; $[\alpha]^{20}D$−8.2; MH$^+$ 524; $^1$H-NMR (DMSO) δ=1.23–1.44 (m, 18H), 2.16 (s, 6H), 3.05–3.41 (m, 4H), 3.79 (m, 1H), 4.29–4.78 (m, 3H), 6.34 (s, 2H), 6.95 (bs, 1H), 7.14 (s, 4H), 8.22 (bs, 1H).

Example 37

This example describes the synthesis of TFA·H-Dmt-Tic-NH-tBu (compound 9 in Table II).

Boc-Dmt-Tic-NH-tBu was treated with TFA as described in Example 3: yield 0.12 g (93%); $R_f(A)$ 0.74; HPLC K'=5.35; mp 150–152° C.; $[\alpha]^{20}D$−15.6; MH$^+$ 424. Anal. ($C_{28}H_{33}N_3O_3$·TFA) C, H, N (C 70.89, H 7.85, N 9.92).

Example 38

This example describes the synthesis of TFA·N,N-(Me)$_2$-Dmt-Tic-NH-tBu (compound 14 in Table II).

This N,N-alkylated peptide was obtained by exhaustive methylation of TFA·H-Dmt-Tic-NH-tBu (compound 9 in Table II) as reported in Example 21: yield 0.12 g (88%); $R_f(A)$ 0.78; HPLC K'=6.01; mp 157–159° C.; $[\alpha]^{20}D$−18.7; MH$^+$ 452. Anal. ($C_{27}H_{37}N_3O_3$·TFA) C, H, N (C 71.81, H 8.26, N 9.30).

Example 39

This example describes the synthesis of Boc-Dmt-Tic-Ala-NH-tBu.

This compound was obtained by condensation of Boc-Dmt-Tic-OH with HCl·H-Ala-OtBu via DCC/HOBt as reported for Boc-Dmt-Tic-Ala-OMe: yield 0.2 g (87%); $R_f(B)$ 0.85; HPLC K'=8.09; mp 150–152° C.; $[\alpha]^{20}D$+28.2; MH$^+$ 595; $^1$H-NMR (DMSO) δ=1.23–1.48 (m, 21H), 2.16 (s, 6H), 3.05–3.41 (m, 4H), 3.79 (m, 1H), 4.29–4.78 (m, 4H), 6.34 (s, 2H), 6.95 (bs, 1H), 7.14 (s, 4H), 8.22 (bs, 1H), 8.36 (bs, 1H).

Example 40

This example describes the synthesis of TFA·Dmt-Tic-Ala-NH-tBu (compound 20 in Table II).

Boc-Dmt-Tic-Ala-NH-tBu was treated with TFA as described in Example 3: yield 0.18 g (91%); $R_f(A)$ 0.64; HPLC K'=5.35; mp 150–152° C.; $[\alpha]^{20}D$+25.7; MH$^+$ 495. Anal. ($C_{28}H_{38}N_4O_4$·TFA) C, H, N (C 67.99, H 7.74, N 11.33).

Example 41

This example describes the synthesis of (R,S)-2-cyano-3-(4-hydroxy-2',6'-dimethylphenyl)-propanoic acid ethyl ester.

Ethyl cyanoacetate (0.62 ml, 7.08 mmol) and, after ten minutes, O-carbethoxy-3,5-dimethyl-4-chloromethylphenol (1.8 g, 7.42 mmol) were added to a solution of sodium ethoxide (Na, 0.17 g, 7.2 mmol; anhydrous EtOH, 12 ml).

The reaction mixture was refluxed for 2 hr, cooled and filtered. The solution was evaporated in vacuo. The residue was crystallized from $H_2O$/acetone (5:1, v/v). The product was purified by column chromatography [$SiO_2$; $Et_2O$/AcOEt (1:1 v/v)]: yield 1.05 g (60%); $R_f$(B) 0.74; HPLC K'=5.38; mp 132–134° C.; MH$^+$ 248; $^1$H-NMR (DMSO) δ=1.25–1.81 (t, 3H), 2.23 (s, 6H), 3.08–3.14 (m, 2H), 4.14–4.27 (m, 3H), 6.44 (s, 2H), 9.17 (s, 1H).

Example 42

This example describes the synthesis of (R,S)-2-cyano-3-(4,hydroxy-2',6'-dimethylphenyl)-propanoic acid.

Sodium hydroxide (1N, 4.68 ml, 4.68 mmol) was added to a solution of (R,S)-2-cyano-3-(4-hydroxy-2',6'-dimethylphenyl)-propanoic acid ethyl ester (1.05 g, 4.24 mmol) in ethanol (10 ml). The reaction mixture was stirred for 24 hr at RT. After evaporation of the solvent, the residue was dissolved in EtOAc and washed with citric acid (10%) and brine. The organic phase was dired and evaporated to dryness. The residue was crystallized from $Et_2O$/PtEt (1:2, v/v): yield 0.79 g (85%); $R_f$(B) 0.31; HPLC K'=3.54; mp 154–156° C.; MH$^+$ 220.

Example 43

This example describes the synthesis of [des-NH2-α-cyano-(R,S)-Dmt]-Tic-OtBu.

HOBt (0.09 g, 0.58 mmol) and DCC (0.12 g, 0.58 mmol) were added to a solution of (R,S)-2-cyano-3-(4-hydroxy-2', 6'-dimethylphenyl)-propanoic acid (0.12 g, 0.53 mmol) and H-Tic-OtBu (0.12 g, 0.53 mmol) in DMF (10 ml) at 0° C. The reaction mixture was stirred for 3 hr at 0° C. and 24 hr at RT. After evaporation of DMF, the residue was treated as reported for Boc-Dmt-Tic-NH-tetrazole-5-yl: yield 0.18 g (80%); $R_f$(B) 0.82; HPLC K'=8.40; mp 140–142° C.; $[α]^{20}$D–13.85; MH$^+$ 435.

Example 44

This example describes the synthesis of [des-NH2-α-cyano-(R,S)-Dmt]-Tic-OH.

[des-NH2-α-cyano-(R,S)-Dmt]-Tic-OtBu (0.18, 0.42 mmol) was treated with TFA (1 ml) for 0.5 hr at RT. Et2O/EtPt (1:1, v/v) was added until the product precipitated: yield 0.15 g (96%); $R_f$(A) 0.68; HPLC K'=5.55; mp 142–144° C.; [α]20D–15.31; MH+ 379; IR (KBr) 3420 (OH), 2360 (nitrile), 1636 (C=O, amide), 1734 (C=O, acid), 1142 cm$^{-1}$ (C—O, carboxylate anion).

Example 45

This example describes the synthesis of αH(R,S)-Dmt-Tic-OH (compound 2 in Table II).

HCl (1 N, 4.5 ml) and PtO2 (0.05 g) were added to a solution of [des-NH2-α-cyano-(R,S)-Dmt]-Tic-OH (0.15 g, 0.4 mmol) in EtOH (30 ml) and H2 bubbled for 8 hr at RT. After filtration, the solution was evaporated to dryness. The residue was crystallized from $Et_2O$/PtEt (1:1, v/v): yield 0.15 g (98%); $R_f$(A) 0.39; HPLC K'=2.51; mp 157–159° C.; $[α]_{20}$D–18.7; MH$^+$ 383; IR (KBr) 3432 (NH$_3^+$), 1683 (C=O, amide), 1616 (C=O, carboxylate anion), 1203 (C—O, carboxylate anion) cm$^{-1}$. Anal. ($C_{22}H_{26}N_2O_4$·TFA) C, H, N (C 69.09, H 6.85, N 7.32).

Example 46

This example describes the synthesis of N,N(Et)2-Dmt-Tic-OH (compound 17 in Table II).

To a stirred solution of TFA·H-Dmt-Tic-OH (0.27 g, 0.56 mM) in CH3CN (10 ml) was added CH3CHO (0.147 ml, 4.26 mM) followed by sodium cyanoborohydride (0.829 g, 1.32 mM). Glacial acetic acid (0.11 ml) was added over 10 min and the reaction was stirred at room temperature for 2hr. The reaction mixture was poured into 100 ml of ethyl acetate and then washed with brine. The organic solvent was dried ($Na_2SO_4$) and evaporated in vacuo to give the crude product that was purified by preparative HPLC: yield 0.26 g (90%); $R_f$0.73; HPLC K'=4.18; mp 117–119; [a]D20–120; MH+ 425. Reference and analytical determinations as in Salvadori et al., *J. Med. Chem.* 40: 3100–3108 (1997).

Example 47

This example describes the binding of the compounds of the present invention to δ-opioid receptors and μ-opioid receptors.

The present inventive compounds were assayed with a rat brain synaptosomal preparation (P2) that had been preincubated in 0.1 M NaCl, 0.4 mM GDP, 50 mM HEPES, pH 7.5, and 50 g/ml soybean trypsin inhibitor for 60 min at RT to remove endogenous opioids (Lazarus et al., *J. Biol. Chem.* 264: 354–362 (1989)). The assays were conducted as previously described (Salvadori et al. (1995), supra; Salvadori et al. (1997), supra; and Lazarus et al., *Eur. J. Med. Chem.* 27: 791–797 (1992)). Briefly, the agonists [$^3$H]DPDPE (30–60 Ci/mmol, NEN-DuPont) and [$^3$H]DAGO (30–60 Ci/mmol, Amersham) were used to label δ and μ sites, respectively, under saturation binding conditions (2 hrs at 22° C.). Excess unlabeled peptide (2 μM) established nonspecific binding levels and the labeled membranes were rapidly filtered on Whatman GF/C glass fibre filters, thoroughly washed, dried and measured for radioactivity using CytoScint (ICN, Irvine, Calif.). The δ antagonist [$^3$H]N,N-($CH_3$)$_2$-Dmt-Tic-OH was catalytically dehalogenated from a diiodo-intermediate to a specific activity of 59.88 Ci/mol and binds to δ receptors with a $K_d$=0.39 nM (Kertesz et al., *J. Label. Compds. Radiopharmac.* 41: 1083–1091 (1998)). The receptor binding and biological properties of the unlabeled peptide were previously described (Salvadori et al. (1997), supra). All analogues were analyzed in duplicate using 5–9 dosages and at least three independent repetitions using different synaptosomal preparations were conducted for each peptide (actual n values are listed in Table II in parentheses) with results given as mean±SEM. The affinity constants ($K_i$) were calculated according to Cheng and Prusoff (*Biochem. Pharmacol.* 22: 3099–3108 (1973)).

As shown in Table II, the elimination of the carboxylate function of H-Dmt-Tic-OH substantially increased the μ affinity of di- and tripeptide derivatives (see compounds 6–16 and 18–21). The net effect was the loss of δ-opioid selectivity and the appearance of compounds that were either essentially nonselective (compounds 6, 9, 10 and 15), weakly μ selective (compounds 8, 11 and 16), or moderately μ selective (compound 12). The δ affinity generally remained high for most C-terminally modified analogues with $K_i$ values ranging from 0.07 to 1 nM. Nonetheless, the binding data revealed that several analogues lost high δ affinity, in particular the methyl ester derivative (compound 8) and those containing the D-Tic enantiomer (compounds 12 and 16).

Interposing a methylene spacer (see compound 1) between the $C_α$ of the Tic residue and the carboxylate function (see Table I) to prevent diketopiperazine formation had minimal effect on δ affinity, but enhanced μ affinity. The same chemical approach employing a methylene group between the amino group and the $C_\alpha$ of Dmt (compound 2) was more detrimental as compared to H-(R,S)Dmt-Tic-OH. The dipeptide analogues containing hydrazide (compound 6), methyl amide (compound 7), and tetrazole-5-yl (compound 10) exhibited high δ affinities, but each with a marked gain in μ affinity, which was also observed with the Ala-containing tripeptide methyl ester (compound 19) relative to its title compound (H-Dmt-Tic-Ala-$NH_2$).

The largest increase in μ affinity occurred in the Dmt-Tic analogues C-terminally substituted with either tert-butyl amide (compounds 9 and 14) or 1-adamantyl amide (compounds 11, 12, 15, 16 and 21). In comparison to H-Dmt-Tic-OH, the μ affinity of compound 15 rose nearly 2,200-fold relative to N,N(Me)$_2$-Dmt-Tic-OH. Comparisons between the amidated parental peptides to their C-terminal derivatives, however, indicated smaller changes in μ affinities.

N-alkylation of Dmt-Tic with piperidine-1-yl (compound 3), pyrrolidine-1-yl (compound 4) or pyrrole-1-yl groups (compound 5) (see Table II) decreased δ affinity, particularly the latter compound whose receptor binding was comparable to H-αDmt-Tic-OH (compound 2), H-Dmt-Tic-OMe (compound 8), and H-Dmt-D-Tic-NH-1-adamantane (compound 12). In spite of the bulky N-terminal substituents, the δ selectivities of compounds 3 and 4 were analogous to other modified peptides.

Receptor binding with the δ antagonist [$^3$H]N,N-(Me)$_2$-Dmt-Tic-OH yielded similar $K_i$ values to those obtained with the agonist [$^3$H]DPDPE in over 80% of the peptides listed in Table II. Exceptions (i.e., peptides whose $K_i$ values differed by at least an order of magnitude) were the title peptide H-Dmt-Tic-OH, which is relatively unstable and forms a diketopiperazine (Marsden et al., *Int. J. Pept. Prot. Res.* 41: 313–316 (1993); Carpenter et al., *J. Am. Chem. Soc.* 116: 8450–8458 (1994); Caspasso et al., *Int. J. Pept. Prot. Res.* 45: 567–573 (1995); and Balboni et al., *Biol. Chem.* 378: 19–29 (1997)) and analogues (compounds 2, 6, 8 and 10).

TABLE I

| Compound No. | R' | Compound No. | R" |
|---|---|---|---|
| 2 | H$_2$NH$_2$C— | 1 | —CH$_2$COOH |
| 3 | piperidin-1-yl | 2–5, 17 | —COOH |
| 4 | pyrrolidin-1-yl | 6 | —CONHNH$_2$ |
| 5 | pyrrol-1-yl | 7, 13 | —CONHCH$_3$ |
| 1, 6–12, 18–21 | H$_2$N— | 8 | —COOCH$_3$ |
| 13–16, 22 | (H$_3$C)$_2$N— | 9, 14 | —CONH—C(CH$_3$)$_3$ |
| 17 | (H$_3$CH$_2$C)$_2$N— | 10 | —CONH-tetrazol-5-yl |

TABLE I-continued

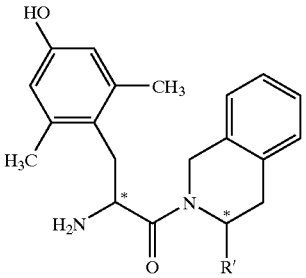

| Compound No. | R' | Compound No. | R" |
|---|---|---|---|
| | | 11, 12, 15, 16 | —CONH—(adamantyl) |
| | | 18 | —CO-Ala—NHCH$_3$ |
| | | 19 | —CO-Ala—OCH$_3$ |
| | | 20 | —CO-Ala—NH—C(CH$_3$)$_3$ |
| | | 21 | —CO-Ala—NH—(adamantyl) |
| | | 22 | —C(OH)—N(H)—C(CH$_3$)$_3$ |

With respect to Table I, the bold numbers refer to the analogues in Table II. Asterisks denote chiral centers.

TABLE II

MEMBRANE RECEPTOR BINDING OF THE MODIFIED DMT-TIC PHARMACOPHORE

| Compound No. | Peptide | K$_i$δ(nM) [$^3$H]DPDPE | [$^3$H]N,N(CH$_3$)$_2$-Dmt-Tic-OH | K$_{iμ}$ (nM) [$^3$H]DAGO | Agonist K$_1$μ/K$_i$δ | Antagonist K$_1$μ/K$_i$δ |
|---|---|---|---|---|---|---|
| | | | Parental Compounds | | | |
| | H-Dmt-Tic-OH | 0.022 ± 0.002(6) | 0.34 ± 0.05 (4) | 3320 ± 435 (7) | 150800$^a$ | 9852 |
| | H-Dmt-Tic-NH$_2$ | 1.22 ± 0.09 (6) | 2.13 ± 0.12 (3) | 277 ± 26 (3) | 227$^a$ | 130 |
| | H-Dmt-Tic-Ala-OH | 0.29 ± 0.03 (6) | 0.29 ± 0.05 (3) | 813 ± 68 (4) | 2852$^a$ | 2784 |
| | H-Dmt-Tic-Ala-NH$_2$ | 0.24 ± 0.02 (5) | 0.69 ± 0.13 (3) | 47 ± 3.4 (4) | 195$^a$ | 68 |
| | N,N(Me)$_2$-Dmt-Tic-OH | 0.12 ± 0.02 (3) | 0.07 ± 0.01 (4) | 2435 ± 462 (3) | 20636$^b$ | 34785 |
| | H-(R,S)Dmt-Tic-OH | 0.46 ± 0.001 (3) | 0.80 ± 0.19 (4) | 1158 ± 327 (3) | 2517 | 1449 |
| | cyclo (DMT-Tic) | 9.58 ± 1.98 (3–5) | | no activity | 635 ± 69 (3–5) | no activity |
| | | | Dipeptide Derivatives | | | |
| 1 | H-Dmt-βTic-OH | 0.85 ± 0.20 (5) | 0.71 ± 0.04 (3) | 418 ± 86 (3) | 498 | 590 |
| 2 | H-αDmt-Tic-OH | 11.2 ± 3.5 (3) | 475 ± 37 (4) | 1740 ± 16 (3) | 155 | 4 |
| 3 | [des-NH$_2$-α-piperidine-1-yl]-Dmt-Tic-OH | 1.18 ± 0.10 (3) | 0.74 ± 0.30 (3) | 2039 ± 264 (3) | 1728 | 2755 |
| 4 | [des-NH$_2$-α-pyrrolidine-1-yl]-Dmt-Tic-OH | 1.62 ± 0.19 (3) | 1.42 ± 0.14 (3) | 814 ± 65 (3) | 502 | 573 |
| 5 | [des-NH$_2$-α-pyrrole-1-yl]-Dmt-Tic-OH | 16.6 ± 2.5 (5) | 9.94 ± 2.5 (3) | 5591 ± 411 (3) | 338 | 562 |
| 6 | H-Dmt-Tic-NHNH$_2$ | 0.99 ± 0.04 (3) | 42.0 ± 7.9 (5) | 85.1 ± 7.3 (3) | 86 | 2 |
| 7 | H-Dmt-Tic-NHMe | 0.47 ± 0.09 (3) | 1.24 ± 0.15 (4) | 85.5 ± 7.7 (3) | 182 | 69 |
| 8 | H-Dmt-Tic-OMe | 9.64 ± 2.2 (3) | 500 ± 90 (5) | 423 ± 25 (3) | 44 | 0.8 |

TABLE II-continued

MEMBRANE RECEPTOR BINDING OF THE MODIFIED DMT-TIC PHARMACOPHORE

| Compound No. | Peptide | $K_i\delta$(nM) [³H]DPDPE | [³H]N,N(CH₃)₂ - Dmt-Tic-OH | $K_{i\mu}$ (nM) [³H]DAGO | Agonist $K_i\mu/K_i\delta$ | Antagonist $K_i\mu/K_i\delta$ |
|---|---|---|---|---|---|---|
| 9  | H-Dmt-Tic-NH-tBu                      | 0.43 ± 0.07 (5)   | 0.93 ± 0.15 (4)  | 5.96 ± 0.82 (4)   | 14             | 6           |
| 10 | H-Dmt-Tic-NH-tetrazole-5-yl           | 0.70 ± 0.03 (3)   | 9.75 ± 1.73 (5)  | 37.0 ± 4.5 (3)    | 53             | 4           |
| 11 | H-Dmt-Tic-NH-1-adamantane             | 0.26 ± 0.05 (4)   | 1.01 ± 0.26 (3)  | 0.76 ± 0.05 (4)   | 3              | 0.8         |
| 12 | H-Dmt-D-Tic-NH-1-adamantane           | 24.5 ± 4.9 (6)    | 70.3 ± 7.25 (3)  | 0.26 ± 0.08 (4)   | 0.01           | 0.004       |
| 13 | N,N(Me)₂-Dmt-Tic-NHMe                 | 0.54 ± 0.07 (3)   | 0.28 ± 0.02 (3)  | 359 ± 62 (3)      | 669            | 1268        |
| 14 | N,N(Me)₂-Dmt-Tic-NH-tBu               | 0.61 ± 0.02 (3)   | 0.11 ± 0.04 (3)  | 226 ± 21 (3)      | 369            | 2132        |
| 15 | N,N(Me)₂-Dmt-Tic-NH-1-adamantane      | 0.16 ± 0.17 (3)   | 0.12 ± 0.02 (3)  | 1.12 ± 0.10 (3)   | 7              | 9           |
| 16 | N,N(Me)₂-Dmt-D-Tic-NH-1-adamantane    | 140 ± 30 (6)      | 120 ± 25.9 (3)   | 50.5 ± 2.6 (3)    | 0.36           | 0.42        |
| 17 | N,N(Et)₂-DMT-Tic-OH                   | 0.92 ± 0.19 (3–5) |                  | not tested        | 35.3 ± 1.96 (3–5) | not tested |
| 18 | H-Dmt-Tic-Ala-NHMe                    | 0.058 ± 0.01 (3)  | 0.12 ± 0.04 (3)  | 5.75 ± 0.72 (3)   | 100            | 47          |
| 19 | H-Dmt-Tic-Ala-OMe                     | 0.23 ± 0.09 (3)   | 0.14 ± 0.04 (3)  | 11.3 ± 1.87 (3)   | 48             | 83          |
| 20 | H-Dmt-Tic-Ala-NH-tBu                  | 0.066 ± 0.01 (3)  | 0.08 ± 0.02 (3)  | 4.03 ± 0.21 (3)   | 61             | 48          |
| 21 | H-Dmt-Tic-Ala-NH-1-adamantane         | 0.073 ± 0.02 (3)  | 0.04 ± 0.01 (3)  | 2.52 ± 0.56 (4)   | 35             | 72          |

With respect to Table II, the numeric value in the parentheses indicates the number (n) of repetitions of independent binding assays using different synaptosomal preparations. [a]Salvadori et al. (1995), supra. [b]Salvadori et al. (1997), supra.

Example 48

This example describes the functional bioactivity of the present inventive compounds.

The functional bioactivity of the present inventive compounds was assessed using standard functional bioassays of δ and μ activity in MVD and GPI (Salvadori et al. (1995), supra; and Salvadori et al., J. Med. Chem. 36: 3748–3756 (1993)). Briefly, a 2–3 cm segment of GPI was placed in a 20 ml tissue bath containing Kreb's solution, 70 μM hexamethonium bromide and 0.125 μM mepyramine and aerated with 95% O₂/5% CO₂ at 36° C. Transmural stimulation of GPI was by means of a square-wave electrical pulse of 0.5 ms duration at a frequency of 0.1 Hz. A single MVD was suspended in 4 ml modified Kreb's solution aerated with 95% O₂/5% CO₂ at 33° C. An isometric transducer recorded the twitch induced by field stimulation (0.1 Hz for 1 ms at 40 V). Dose-response curves were obtained (Salvadori et al. (1995), supra) for both tissues. The μ agonist activity was compared against dermorphin ($IC_{50}$=1.82 nM) and δ antagonism was determined through the inhibition of deltorphin C ($\delta_1$ receptor agonist, $IC_{50}$=0.54 nM) in comparison to the nonpeptide δ antagonist naltrindole. Data were derived from at least four independent tissue samples and dose-response curves from which the $pA_2$ values were determined (Salvadori et al. (1997), supra) according to Arunlakshana and Schild (Br. J. Pharmacol. 14: 48–58 (1959)). In other words, antagonism was expressed as $pA_2$ (negative logarithm of the concentration that causes 50% inhibition) and agonism was expressed as the $IC_{50}$.

Dmt-Tic analogues (compounds 1, 9, 13, 15, 20 and 21) demonstrated the highest δ-antagonist functional bioactivities (Table III) as well as some of the highest δ-receptor affinities (Table II). Of greater interest, however, was the observation that several analogues acquired unusual bioactivity profiles. For example, both of compounds 13 and 15 elicited excellent δ antagonism, yet the former was a weak μ antagonist and the latter clearly displayed μ agonism (Table III). Inclusion of the D-Tic enantiomer (compounds 12 and 16) essentially greatly reduced bioactivity on MVD with μM activity on GPI. Replacement of the N-terminal amine through alkylation by piperidine-1-yl (compound 3), pyrolidine-1-yl (compound 4) or pyrrole-1-yl (compound 5) was detrimental for all bioactivity measurements on MVD (Table III). N-alkylation by methyl groups to form secondary or tertiary amines was the only N-terminal substitution tolerated (Lazarus et al. (1998), supra; see Table III). Interestingly, the non-alkylated, C-terminally modified dipeptides, i.e., compounds 11 and 12, lacked δ antagonism; however, compound 11 surprisingly manifested a weak δ agonism and moderate μ agonism in spite of its high δ affinity (see Table II), while other analogues, i.e., compounds 7, 13, 14 and 18, also produced anomalous biological activities on MVD and GPI (see Table III) relative to their receptor binding parameters (see Table II). H-Dmt-Tic-NHMe (compound 7) had extraordinarily weak δ agonism with low μ antagonism, while its Ala-tripeptide derivative (compound 18) gave very weak δ and μ agonism. Despite the high δ-receptor affinity of compound 14, the bioactivity data indicated only modest δ antagonism and weak μ antagonism. The tetrazole-5-yl-amide analogue (compound 10) was a weak δ antagonist with very minimal activity on GPI (see Table III).

TABLE III

FUNCTIONAL BIOACTIVITY OF THE MODIFIED DMT-TIC PHARMACOPHORE

| Compound No. | Peptide | MVD $pA_2$ (range) | $K_e$(nM) | $ED_{50}(\mu M)$ | GPI $pA_2$ (range) | $K_e(\mu M)$ | $ED_{50}(\mu M)$ |
|---|---|---|---|---|---|---|---|
|  | H-Dmt-Tic-OH     | 8.2 | 5.7 | — | — | — | >10[a] |
|  | H-Dmt-Tic-NH₂    | 7.2 | 42  | — | — | — | >10[a] |
|  | H-Dmt-Tic-Ala-OH | 8.4 | 4.0 | — | — | — | >10[a] |

TABLE III-continued

FUNCTIONAL BIOACTIVITY OF THE MODIFIED DMT-TIC PHARMACOPHORE

| Compound No. | Peptide | MVD pA$_2$ (range) | K$_e$(nM) | ED$_{50}$($\mu$M) | GPI pA$_2$ (range) | K$_e$($\mu$M) | ED$_{50}$($\mu$M) |
|---|---|---|---|---|---|---|---|
| | H-Dmt-Tic-Ala-NH$_2$ | 8.0 | 9.0 | — | — | — | 4.74 ± 0.9 |
| | N,N(Me)$_2$-Dmt-Tic-OH | 9.4 | 0.28 | — | — | — | >10$^b$ |
| | H-(R,S)Dmt-Tic-OH | 8.17 (7.8–8.6) | 6.76 | — | — | — | >10 |
| | cyclo (DMT-Tic) | 5.43 | | | | | |
| 1 | H-Dmt-βTic-OH | 8.8 (8.6–9.1) | 1.41 | — | — | — | >10 |
| 3 | [des-NH$_2$-α-piperidine-1-yl]-Dmt-Tic-OH | 7.31 (7.15–7.47) | 49 | — | — | — | >10 |
| 4 | [des-NH$_2$-α-pyrrolidine-1-yl]-Dmt-Tic-OH | 6.9 (6.9–7.1) | 121 | — | — | — | >10 |
| 5 | [des-NH$_2$-α-pyrrole-1-yl]-Dmt-Tic-OH | 6.39 (6.0–6.7) | 408 | — | — | — | >10 |
| 7 | H-Dmt-Tic-NHMe | —$^d$ | >10,000 | 21.2 (9.0–45) | 5.94 (4.2–7.6) | 1.15 | >10 |
| 9 | H-Dmt-Tic-NH-tBu | 8.24 (8.2–8.5) | 1.74 | — | — | — | 1.04 (0.69–1.5) |
| 10 | H-Dmt-Tic-NH-tetrazole-5-yl | 7.44 (7.1–7.7) | 36.3 | — | — | — | 8.2 (2.7–24.9) |
| 11 | H-Dmt-Tic-NH-1-adamantane | — | >10,000 | 0.87 (0.8–1.2) | — | — | 0.036 (0.019–0.068) |
| 12 | H-Dmt-D-Tic-NH-1-adamantane | — | >10,000 | — | — | — | 1.68 (1.23–2.3) |
| 13 | N,N(Me)$_2$-Dmt-Tic | 9.39 (8.8–9.9) | 0.41 | — | 6.41 (6.3–6.5) | 0.39 | >10 |
| 14 | N,N(Me)$_2$-Dmt-Tic-NH-tBu | 7.85 (7.5–8.1) | 14.1 | — | .52 (6.2–6.7) | 0.30 | >10 |
| 15 | N,N(Me)$_2$-Dmt-Tic-NH-1-adamantane | 9.06 (8.6–9.5) | 0.87 | — | — | — | 0.016 (0.011–0.023) |
| 16 | N,N(Me)2-Dmt-D-Tic-NH-1-adamantane | 6.91 (6.8–7.0) | 128 | — | — | — | 4.48 (3.17–6.32) |
| 17 | N,N(Et)$_2$-Dmt-Tic-OH | not tested | | | not tested | | |
| 18 | H-Dmt-Tic-Ala-NHMe | — | — | 1.29 (1.18–1.42) | — | — | 0.29 (0.18–0.45) |
| 20 | H-Dmt-Tic-Ala-NH-tBu | 9.16 (8.7–9.5) | 0.69 | — | 6.76 (6.6–6.9) | 0.17 | >10 |
| 21 | H-Dmt-Tic-Ala-NH-1-adamantane | 9.29 (9.0–9.5) | 0.51 | — | — | — | 1.0 (0.7–3.0) |

With respect to Table III, data were derived from at least four (at least three for compounds 17 and 18) independent tissue samples and dose-respone curves. pA$_2$ is the mean and the range is in parentheses. $^a$Salvdori et al. (1995), aupra. $^b$Salvadori et al. (1997), supra. $^c$Temussi et al. (1994), supra. $^d$A dash indicates the absence of pharmacological activity.

Example 49

This example describes the ability of certain compounds of the present invention to inhibit hMDR-1.

Stably transfected G-185 fibroblasts containing hMDR-1 and NIH 3T3 cell lines were grown to confluent monolayers in DMEM containing 4.5 g glucose/1, 10% fetal calf serum, L-glutamine, penicillin (50 units/ml), streptomycin (50 $\mu$g/ml) and 1 mM sodium pyruvate in 5% CO$_2$ at 37° C. G-185 cells were maintained in 60 ng/l colchicine.

The assay for Pgp is based on the diffusion of non-fluorescent calcein AM across the cell membrane. Calcein AM is then hydrolyzed and accumulates as the fluorescent calcein. In transfected cells expressing excess hMDR-1, Pgp extrudes calcein AM from the cell before hydrolysis occurs; inhibition of hMDR-1 results in the accumulation of intracellular calcein. Transfected G-185 cells and the NIH 3T3 cells were analyzed in triplicate using seven graded dosages of verapamil or the opioid peptides in 96-well plates. Cells (2.5×10$^6$/well) were incubated in 100 $\mu$l culture medium for 15 min at 37° C. and 50 $\mu$l of 1 $\mu$M calcein AM in PBS, plus 50 $\mu$l of verapamil or one of the present inventive compounds in PBS, or 100 $\mu$l of PBS alone (control) were added. Cells were mixed and incubated for 15 min at 37° C., then centrifuged for 5 min at 2,000×g, and then washed three times in 200 $\mu$l PBS. Cell pellets were resuspended in 200 $\mu$l PBS and transferred to white Microfluor Plates (Nunc, Copenhagen, Denmark) in order to measure calcein-specific fluorescence (494 nm absorption; 517 nm emission). Internal controls were carried out with each experiment using verapamil and PBS in order to compare the consistency between cell preparations. Means±SE (error bars) were determined and plotted using Prism™ (GraphPad, San Diego, Calif.).

Figure 1:
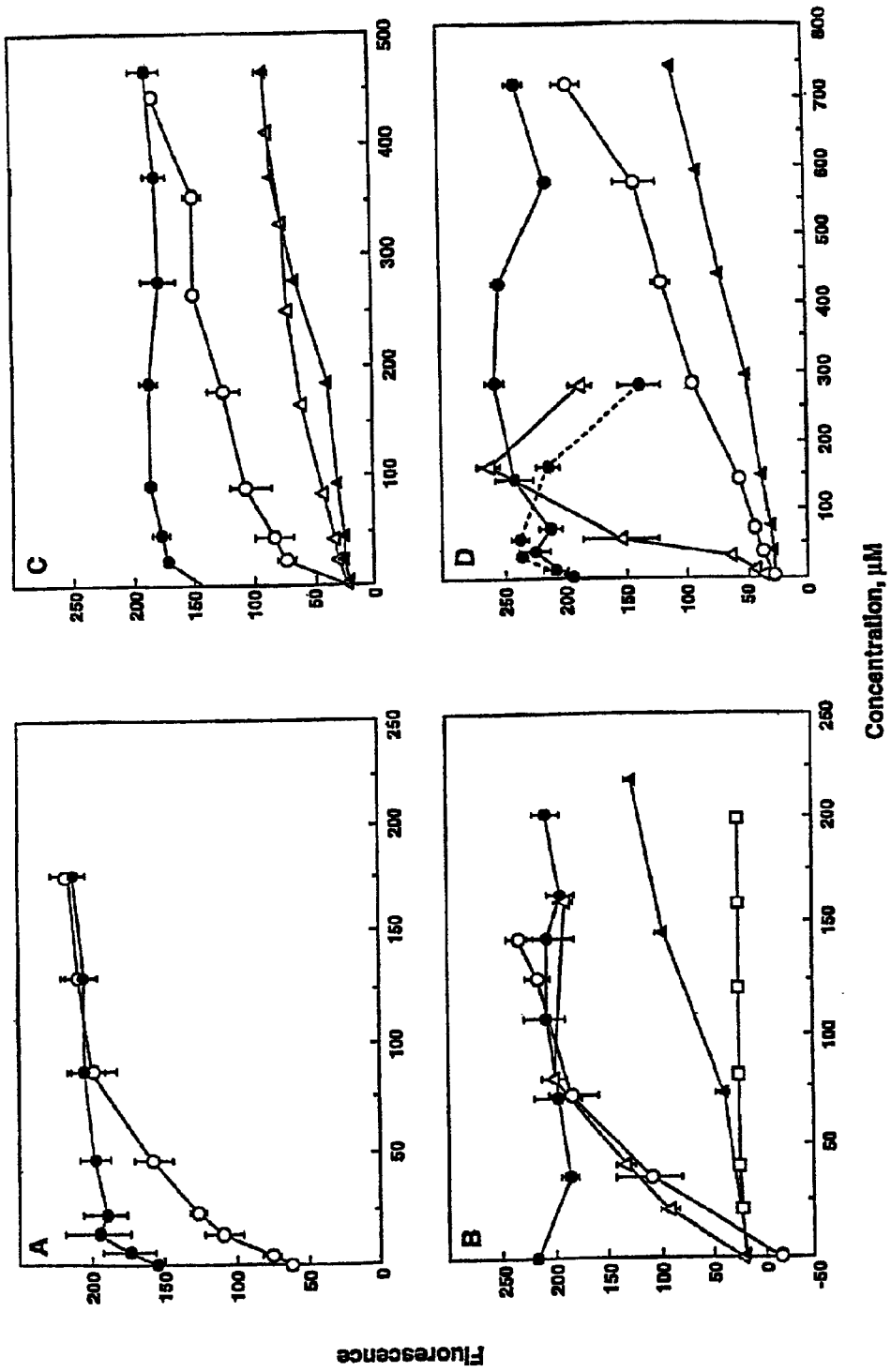
FIG. 1A is a graph of fluorescence vs. concentration ($\mu$M).
FIG. 1B is a graph of fluorescence vs. concentration ($\mu$M).
FIG. 1C is a graph of fluorescence vs. concentration ($\mu$M).
FIG. 1D is a graph of fluorescence vs. concentration ($\mu$M).

The results are shown in FIGS. 1A–1D, all of which are graphs of fluorescence vs. concentration ($\mu$M). In FIG. 1A, the inhibition of hMDR-1 in G-185 cells (○) and NIH 3T3 cells (•) by verapamil (control) is shown. In FIG. 1B, the inhibition of hMDR-1 in G-185 cells with NIH 3T3 cells (•) by the 1-adamantyl amide derivatives N,N(Me)$_2$-Dmt-Tic-NH-1-adamantane (compound 15) (○), H-Dmt-Tic-NH-1-adamantane (compound 11) (Δ), H-Dmt-Tic-Ala-NH-1-adamantane (compound 12) (▲), and N,N(Me)$_2$-Dmt-Tic-OH (□) is shown. In FIG. 1C, the inhibition of hMDR-1 in G-185 cells with NIH 3T3 cells (•) by the tert-butyl amide derivatives NN(Me)$_2$-Dmt-Tic-NH-tBu (compound 14) (○), H-Dmt-Tic-Ala-NH-tBu (compound 20) (Δ), and H-Dmt-Tic-NH-tBu (compound 9) (▲) is shown. In FIG. 1D, the inhibition of hMDR-1 in NIH 3T3 cells (•) and with naltrindole (• - - - •) or in G-185 cells with naltrindole (Δ), cyclo(Dmt-Tic) (○) or N,N-(Et)2-Dmt-Tic-OH (compound 17) (▲) is shown.

Inhibition of Pgp in G-185 fibroblasts occurred in a dose-response manner with Dmt-Tic dipeptides containing 1-adamantyl amide and with or without N-alkylation (FIG. 1B) comparable to verapamil (FIG. 1A). Peptides lacking N- or C-terminal hydrophobic substituents (FIG. 1A, deltorphin B, deltorphin A, DER, DAGO, DPDPE, DAMME, DtMe, DPD, [Trp$^4$,Tyr$^5$]DER, [Trp$^4$,Lys-OH$^7$]DER, DSB, DTA, PipDTOH and MeDTOH) were inactive. The maximum effective dose of the peptides and verapamil fell within the range of 75–100 $\mu$M. In contrast, NIH-3T3 fibroblasts lacking membrane Pgp-1 were unresponsive. The spatially confined aromatic rings of Dmt-Tic and the saturated rings of 1-adamantane presented an optimal configuration to support the inhibition of hMDR-1 activity, which is diminished by inclusion of the anion function that determines δ-receptor selectivity. The order of inhibition by 1-adamantyl amide derivatives was: N,N(Me)$_2$-Dmt-Tic-NH-1-adamantane (compound 15)=H-Dmt-Tic-NH-1-adamantane (compound 11)>H-Dmt-Tic-Ala-NH-1-adamantane (compound 21)>>N,N(Me)₂-Dmt-Tic-OH (inactive). These results clearly demonstrate that inhibition of hMDR-1 only occurs in the presence of Dmt-Tic modified with hydrophobic groups. Fortuitously, H-Dmt-Tic-NH-1-adamantane (compound 15) only exhibited weak biological activities (Table III) and, thus, may function as a "chemosensitizer" without side effects on the δ- or μ-opioid systems.

Although the 1-adamantyl amide derivative of Dmt-Tic enhanced the inhibition of hMDR-1, incorporation of Ala³-NH-1 -adamantyl-amide curtailed activity (see FIG. 1B). These observations suggest that distance between hydrophobic and aromatic centers in the peptide play a definitive role in the interaction with hMDR-1, and that the inhibitor effectiveness of the Dmt-Tic compounds was independent of their receptor binding activities or pharmacological bioactivites (Table III). A reduction in the hydrophobicity at the C-terminus by the graded reduction in hydrophobicity from 1-adamantyl amide to tert-butyl amide and methyl amide (see FIG. 1C) was comparable to the diminution of activity in dipyridamole analogues containing only a single methyl group. The order of activity by tert-butyl amide substances was: N,N(Me)₂-Dmt-Tic-NH-tBu (compound 14)>H-Dmt-Tic-Ala-NH-tBu (compound 20)>H-Dmt-Tic-NH-tBu (compound 9)>>H-Dmt-Tic-NHMe (compound 7) (inactive). In the case of tert-butyl amide derivatives, the additional hydrophobicity afforded by N-alkylation by methyl groups increased the inhibition of hMDR-1 (see FIG. 1C). While N,N(Me)₂-Dmt-Tic-OH was inactive, N-alkylation by ethyl groups increased the inhibition of hMDR-1, but substantially less than that observed with the tert-butyl amide or 1-adamantyl amide conjugates (see FIG. 1D). Interestingly, the elevation in hydrophobicity associated with N-alkylation of the Dmt-Tic pharmacophore enhanced δ antagonism in vitro by 20-fold without significant changes on δ-opioid binding parameters. On the other hand, 1-adamantyl amide or tert-butyl amide increased μ-receptor binding without interfering with δ-receptor interactions to produce non-selective or μ-selective opioid peptides.

The spontaneous formation of the diketopiperazine, cyclo (Dmt-Tic), was a moderately effective inhibitor of hMDR-1 (see FIG. 1D). These results with cyclo(Dmt-Tic) call into question the requirement for a tertiary amine for Pgp inhibition. On the other hand, the non-peptide δ antagonist naltrindole exhibited inhibition that dissipated at high concentrations (see FIG. 1D), which suggests possible disruption of membrane integrity. The lack of inhibition with opioid agonists, such as dermorphin, deltorphin and the enkephalin analogues DAGO, DPDPE and DAMME, indicates that the charged function retards passage through the BBB. Thus, the data indicate that enhancing the hydrophobicity of Dmt-Tic analogues in order to accelerate passage through the BBB also makes them better substrates for Pgp. Specifically, the covalent addition of tert-butyl amide or 1-adamantyl amide converts a potent opioid antagonist into an inhibitor of hMDR-1. The fact that H-Dmt-Tic-NH-1-adamantane (compound 15) exhibits minimal bioactivity would make it an erstwhile candidate as a chemosensitizer for chemotherapy of cancers containing hMDR-1.

Example 50

This example describes the synthesis of (1H-Benzimidazol-2-yl-methyl)-carbamic acid tert-butyl ester (Boc-NH—CH2-Bid).

A solution of Boc-Gly-OH (1.7 g, 9.6 mmol) and NMM (1 ml, 9.6 mmol) in DMF (10 ml) was treated at −20° C. with isobutyl chloroformate (IBCF) (1.2 ml, 9.6 mmol). After 10 min at −20° C., o-phenylendiamine (1 g, 9.6 mmol) was added. The reaction mixture was allowed to stir while slowly warming to room temperature (1 h) and then stirred for an additional 3 h.

The solvent was evaporated and the residue was partitioned between EtOAc and H2O. The EtOAc layer was washed with 5% NaHCO3 and brine and dried over Na2SO4. The solution was filtered, the solvent evaporated and the residual solid dissolved in glacial acetic acid (10 ml). The solution was heated at 65° C. for 1 h. After evaporation of the solvent, the residue was crystallized from Et₂O/Pe (1:9, v/v): yield 2.11 g. (89%); Rf(B) 0.43; HPLC K'=3.95; mp 131–133° C.; MH⁺ 248; ¹H-NMR (DMSO) δ=1.40 (s, 9H), 4.22–4.40 (m, 2H), 7.26–7.70 (m, 5H), 7.98 (s, 1H).

Example 51

This example describes the synthesis of Boc-Tic-NH—CH2-Bid.

To a solution of Boc-Tic-OH (0.3 g, 1.08 mmol) and 2 TFA·H-NH—CH2-Bid (Cescon et al., *J. Org. Chem.*, 27: 581–586 (1962)) (0.41 g, 1.08 mmol) in DMF (10 ml) at 0° C. were added NMM (0.24 ml, 2.16 mmol), HOBt (0.18 g, 1.19 mmol) and WSC (0.23 g, 1.19 mmol). The reaction mixture was stirred for 3 h at 0° C. and 24 h at room temperature. After evaporation of DMF, the residue was solubilized in EtOAc and washed with NaHCO3 (5%) and brine. The organic phase was dried and evaporated to dryness. The residue was crystallized from Et2O/Pe (1:9, v/v): yield 0.36 g. (82%); $R_f$(B) 0.68; HPLC K'=8.12; mp 142–144° C.; [α]20D−12.1; MH+ 407; 1H-NMR (DMSO) δ=1.38–1.42 (d, 9H), 3.08–3.15 (m, 2H), 4.22–4.53 (m, 5H), 7.05–7.71 (m, 9H), 7.97 (s, 1H).

Example 52

This example describes the synthesis of 2TFA·H-Tic-NH—CH2-Bid.

Boc-Tic-NH—CH2-Bid (0.36 g, 0.89 mmol) was treated with TFA (1 ml) for 0.5 h at room temperature. Et2O/Pe (1:1, v/v) were added to the solution until the product precipitated: yield 0.46 g (97%); Rf(A) 0.43; HPLC K'=4,11; mp 180–182° C.; [α]20D−14.8; MH+ 307.

Example 53

This example describes the synthesis of Boc-Dmt-Tic-NH—CH2-Bid.

To a solution of Boc-Dmt-OH (0.25 g, 0.82 mmol) and 2TFA-H-Tic-NH—CH2-Bid (0.44 g, 0.82 mmol) in DMF (10 ml) at 0° C. were added NMM (0.18 ml, 1.64 mmol), HOBt (0.14 g, 0.90 mmol) and WSC (0.17 g, 0.90 mmol). The reaction mixture was stirred for 3 h at 0° C. and 24 h at room temperature. After evaporation of DMF, the residue was solubilized in EtOAc and washed with NaHCO₃ (5%) and brine. The organic phase was dried and evaporated to dryness. The residue was crystallized from Et₂O/Pe (1:9, v/v): yield 0.39 g (80%); Rf(B) 0.68; HPLC K'=8.98; mp 142–144° C.; [α]²⁰D−22.5; MH⁺ 598; ¹H-NMR (DMSO) δ=1.32–1.39 (d, 9H), 2.17 (s, 6H), 2.85–3.10 (m, 4H), 4.22–4.65 (m, 6H), 6.37 (s, 2H), 7.05–7.71 (m, 10H), 7.97 (s, 1H).

Example 54

This example describes the synthesis of 2TFA·H-Dmt-Tic-NH—CH2-Bid (compound 24).

Boc-Dmt-Tic-NH—CH2-Bid (0.1 g, 0.17 mmol) was treated with TFA (1 ml) for 0.5 h at room temperature.

Et2O/Pe (1:1, v/v) were added to the solution until the product precipitated: yield 0.12 g (97%); Rf(A) 0.31; HPLC K'=5.40; mp 152–154° C.; $[\alpha]^{20}_D$–35.2; MH+ 499.

Example 55

This example describes the synthesis of (1H-Benzimidazol-2-ylethyl)-carbamic acid tert-butyl ester (Boc-NH—CH2-CH2-Bid).

This product was obtained from Boc-βAla-OH and o-phenylenediamine as reported for Boc-NH—CH2-Bid: yield 0.8 g (85%); Rf(B) 0.52; HPLC K'=4.25; mp 142–144° C.; MH+ 262; 1H-NMR (DMSO) δ=1.38 (s, 9H), 2.81–3.29 (m, 4H), 7.25–7.68 (m, 5H), 7.95 (s, 1H).

Example 56

This example describes the synthesis of Boc-Tic-NH—CH2-CH2-Bid.

This substance was obtained by condensation of Boc-Tic-OH with 2TFA·H2N-CH2-CH2-Bid (Cescon et al., *J. Org. Chem.*, 27: 581–586 (1962)) via WSC/HOBt as reported for Boc-Tic-NH—CH2-Bid: yield 0.36 g (88%); Rf(B) 0.72; HPLC K'=8.38; mp 147–149° C.; [α]20D–10.7; MH+ 421; 1H-NMR (DMSO) δ=1.39–1.41 (d, 9H), 2.80–3.31 (m, 6H), 4.21–4.55 (m, 3H), 7.07–7.69 (m, 9H), 7.99 (s, 1H).

Example 57

This example describes the synthesis of 2TFA·H-Tic-NH—CH2-CH2-Bid.

Boc-Tic-NH—CH2-CH2-Bid was treated with TFA as reported for 2TFA·H-Tic-NH—CH2-Bid: yield 0.35 g (98%); Rf(A) 0.48; HPLC K'=4.18; 176–178° C.; [α]20D–12.3; MH+ 321.

Example 58

This example describes the synthesis of Boc-Dmt-Tic-NH—CH2-CH2-Bid.

This compound was obtained by condensation of Boc-Dmt-OH with 2TFA·H-Tic-NH—CH2-CH2-Bid via WSC/HOBt as reported for Boc-Dmt-Tic-NH—CH2-Bid: yield 0.29 g (83%); Rf(B) 0.72;HPLC K'=9.03; mp 151–153° C.; [α]20D–19.9; MH+ 612; 1H-NMR (DMSO) δ=1.33–1.41 (d, 9H), 2.16 (s, 6H), 2.81–3.31 (m, 4H), 4.22–4.64 (m, 4H), 6.38 (s, 2H), 7.04–7.69 (m, 1OH), 7.98 (s, 1H).

Example 59

This example describes the synthesis of 2TFA·H-Dmt-Tic-NH—CH2-CH2-Bid (compound 25).

Boc-Dmt-Tic-NH—CH2-CH2-Bid was treated with TFA as reported for 2TFA·H-Dmt-Tic-NH—CH2-Bid: yield 0.052 g (87%); $R_f$(A) 0.34; HPLC K'=4.88; mp 156–158° C.; [α]20D–30.7; MH+ 513.

Example 60

This example describes the synthesis of Boc-Gly-NH—CH2-Bid.

This compound was obtained from Boc-Gly-Gly-OH and o-phenylenediamine as reported for Boc-NH—CH2-Bid: yield 0.73 g (82%); $R_f$(B) 0.55; HPLC K'=4.53; mp 148–150° C.; MH+ 305; 1H-NMR (DMSO) δ=1.40–1.42 (d, 9H), 3.85–4.46 (m, 4H), 7.25–7.71 (m, 6H), 7.94 (s, 1H).

Example 61

This example describes the synthesis of 2TFA·H-Gly-NH—CH2-Bid.

Boc-Gly-NH—CH2-Bid was treated with TFA as reported for 2TFA·H2N—CH2-Bid: yield 0.49 g (97%); $R_f$(A) 0.45; HPLC K'=1.88; mp 187–189° C.; MH+ 205.

Example 62

This example describes the synthesis of Boc-Tic-Gly-NH—CH2-Bid.

This substance was obtained by condensation of Boc-Tic-OH with 2TFA·H-Gly-NH—CH2-Bid via WSC/HOBt as reported for Boc-Tic-NH—CH2-Bid: yield 0.38 g (84%); $R_f$(B) 0.73;HPLC K'=8.16; mp 146–148° C.; [α]20D–10.4; MH+ 464; 1H-NMR (DMSO) δ=1.40–1.42 (d, 9H), 3.08–3.15 (m, 2H), 3.85–4.55 (m, 7H), 7.03–7.70 (m, 10H), 7.95 (s, 1H).

Example 63

This example describes the synthesis of 2TFA·H-Tic-Gly-NH—CH2-Bid.

Boc-Tic-Gly-NH—CH2-Bid was treated with TFA as reported for 2TFA·H-Tic-NH—CH2-Bid: yield 0.32 g. (95%); $R_f$(A) 0.47; HPLC K'=4.35; mp 163–165° C.; [α]20D–10.1; MH+ 364.

Example 64

This example describes the synthesis of Boc-Dmt-Tic-Gly-NH—CH2-Bid.

This compound was obtained by condensation of Boc-Dmt-OH with 2TFA·H-Tic-Gly-NH—CH2-Bid via WSC/HOBt as reported for Boc-Dmt-NH—CH2-Bid: yield 0.28 g (85%); $R_f$(B) 0.73; HPLC K'=9.03; mp 146–148° C.; [α]20D–19.3; MH+ 655; 1H-NMR (DMSO) δ=1.35–1.40 (d, 9H), 2.17 (s, 6H), 2.85–3.12 (m, 4H), 4.20–4.72 (m, 8H), 6.37 (s, 2H), 7.05–7.75 (m, 1H), 7.99 (s, 1H).

Example 65

This example describes the synthesis of 2TFA·H-Dmt-Tic-Gly-NH—CH2-Bid (compound 26).

Boc-Dmt-Tic-Gly-NH—CH2-Bid was treated with TFA as reported for 2TFA·H-Dmt-Tic-NH—CH2-Bid: yield 0.068 g (96%); $R_f$(A) 0.35; HPLC K'=4.95; mp 155–157° C.; [α]20D–30.8; MH+ 557.

Example 66

This example describes the synthesis of Boc-Tic-Gly-NH-Ph.

This compound was obtained by condensation of Boc-Tic-OH with TFA·H-Gly-NH-Ph49 as reported for Boc-Tic-NH—CH2-Bid: yield 0.24 g (85%); $R_f$(B) 0.67; HPLC K'=10.73; mp 131–133° C.; [α]20D–36.8; MH+ 410; 1H-NMR (DMSO) δ=1.39–1.41 (d, 9H), 3.08–3.15 (m, 2H), 3.61 (d, 2H), 4.22–4.92 (m, 3H), 6.91–7.31 (m, 10H), 8.96 (bs, 1H).

Example 67

This example describes the synthesis of TFA·H-Tic-Gly-NH-Ph.

Boc-Tic-Gly-NH-Ph was treated with TFA as reported for 2 TFA·H-Tic-NH—CH2-Bid: yield 0.18 g (96%); $R_f$(A) 0.35; HPLC K'=6.07; mp 165–167° C.; [α]20D–32,5; MH+ 310.

Example 68

This example describes the synthesis of Boc-Dmt-Tic-Gly-NH-Ph.

This compound was obtained by condensation of Boc-Dmt-OH with TFA·H-Tic-Gly-NH-Ph as reported for Boc-Dmt-Tic-NH—CH2-Bid: yield 0.14 g (84%); $R_f$(B) 0.64; HPLC K'=9.9; mp 144–146° C.; [α]20D–19.7; MH+ 601; 1H-NMR (DMSO) δ=1.40–1.42 (d, 9H), 2.17 (s, 6H), 3.08–3.15 (m, 4H), 3.61 (d, 2H), 4.22–4.92 (m, 3H), 6.37 (s, 2H), 6.91–7.31 (m, 11H), 8.94 (bs, 1H).

Example 69

This example describes the synthesis of TFA·H-Dmt-Tic-Gly-NH-Ph (compound 27).

Boc-Dmt-Tic-Gly-NH-Ph was treated with TFA as reported for 2 TFA·H-Dmt-Tic-NH—CH2-Bid: yield 0.07 g (97%); $R_f$(A) 0.41; HPLC K'=7.18; mp 155–7° C.; [α]20D–21.8; MH+ 444.

Example 70

This example describes the synthesis of Boc-Tic-Gly-NH-Bzl.

This compound was obtained by condensation of Boc-Tic-OH with TFA×H-Gly-NH-Bzl50 as reported for Boc-Tic-NH—CH2-Bid: yield 0.26 g. (88%); $R_f$(B) 0.72; HPLC K'=11.02; mp 123–125° C.; [α]20D–35.2; MH+ 424; 1H-NMR (DMSO) δ=1.39–1.41 (d, 9H), 3.08–3.15 (m, 2H), 3.61 (d, 2H), 4.22–4.92 (m, 5H), 6.91–7.31 (m, 10H), 8.25 (t, 1H).

Example 71

This example describes the synthesis of TFA·H-Tic-Gly-NH-Bzl.

Boc-Tic-Gly-NH-Bzl was treated with TFA as reported for 2 TFA×H-Tic-NH—CH2-Bid: yield 0.20 g (97%); $R_f$(A) 0.38; HPLC K'=6.14; mp 151–153° C.; [α]20D–30.8; MH+ 324.

Example 72

This example describes the synthesis of Boc-Dmt-Tic-Gly-NH-Bzl.

This compound was obtained by condensation of Boc-Dmt-OH with TFA×H-Tic-Gly-NH-Bzl as reported for Boc-Dmt-Tic-CH2-Bzl: yield 0.15 g (81%); Rf(B) 0.68; HPLC K'=10.4; mp 138–140° C.; [α]20D–18.9; MH+ 615; 1H-NMR (DMSO) δ=1.40–1.42 (d, 9H), 2.17 (s, 6H), 3.08–3.15 (m, 4H), 3.61 (d, 2H), 4.22–4.92 (m, 5H), 6.37 (s, 2H), 6.91–7.31 (m, 11H), 8.25 (t, 1H).

Example 73

This example describes the synthesis of TFA·H-Dmt-Tic-Gly-NH-Bzl (compound 28).

Boc-Dmt-Tic-Gly-NH-Bzl was treated with TFA as reported for 2 TFA×H-Dmt-Tic-NH—CH2-Bid: yield 0.07 g (98%); $R_f$(A) 0.44; HPLC K'=7.39; 148–150° C.; [α]20D–20.1; MH+ 516.

Example 74

This example describes radio-receptor assays.

The peptides were assayed in a competition assay under equilibrium conditions with a P2 preparation of rat brain synaptosomes (Lazarus et al., *J. Biol. Chem.*, 264: 354–362 (1989)) using [3H]DPDPE (32.0 Ci/mmol; NEN-DuPont, Bilirica, Mass.) for δ receptors and [3H]DAGO (58.0 Ci/mmol; Amersham, Arlington Heights, Ill.) for μ receptors in 50 mM HEPES, pH 7.5, containing MgCl2 and a cocktail of several protease inhibitors and glycerol (Lazarus et al., *J. Med. Chem.*, 34: 1350–1359 (1991)). After 120 min incubation at room temperature (23–24° C.), the samples were rapidly filtered through Whatman GF/C glass fiber filers and washed three times with 2 ml ice-cold 0.05 M Tris, pH 7.4–7.5, containing 0.1% BSA. Presoaking filters in 0.1% polyethylenimine is only required in assays with peptides carrying an overall positive charge, such as dynorphin or nociceptin (Guerrini et al., *J. Med. Chem.*, 40: 1789–1793 (1997)). Non-specific binding was determined using 2 μM unlabeled DPDPE or DAGO for δ or μ assays, respectively. The $K_i$ data, determined according to Cheng and Prusoff (Cheng et al., *Biochem. Pharmacol.*, 22: 3099–3108 (1973)), represent the means±SE from 3 or more independent assays using at least 3 different synaptosome preparations and testing the analogues with 5–8 graded dosages over 2–3 orders of magnitude in concentration.

The appearance of high δ affinity (Table IV) depends on the quality of the radioligand, either [³H]DPDPE, [³H]DAGO, [³H]N,N(CH₃)₂-Dmt-Tic-OH (Kertesz et al., *J. Labelled Compd. Radiopharmac.*, 41: 1083–1091 (1998); Monory et al., NeuroReport, 11: 2083–2086 (2000)) or [³H]deltorphin B, which all yielded consistently comparable $K_i$ values (Salvadori et al., *J. Med. Chem.*, 42: 5010–5019 (1999); Pagé et al., *J. Med. Chem.*, 44: 2387–2390 (2001)). As long as the synaptosomal preparations are prepared from fresh rat brains and stored at −80° C. in glycerol (Lazarus et al., *J. Biol. Chem.*, 264: 354–362 (1989)), stability and reliability of the radioligand remained the key factor.

The Dmt-Tic pharmacophore peptides (23–28) had exceptionally high δ affinities, in which the $K_i$ values were 0.1 nM or less (Table IV). In Table IV, the Ki values (nM) were determined by Cheng and Prusoff using a rat brain receptor ($P_2$ synaptosome) assay, the mean±SE with n repetitions in parentheses, were determined using Prism™ (GraphPad). Each repetition was an independent bioassay conducted in duplicate using 5–8 graded dosages of peptide; confidence levels are in parentheses. $pA_2$ is the negative log of the molar concentration required to double the agonist concentration to achieve the original response. $pEC_{50}$ is the negative log of the molar concentration of an agonist to produce 50% of the maximum effect. The C-terminal substituents containing a spacer and an aromatic ring substituent exerted essentially minimal influence on δ binding parameters in these analogues; i.e., no linker (23) or containing NH—CH₂ (24), NH—CH₂—CH (25), Gly-NH (27), or Gly-NH—CH₂ (26, 28) were nearly equivalent. The interaction between peptide ligand and μ receptors, on the other hand, demonstrated remarkable variation (Table IV). C-Terminal aromatic groups enhanced μ-receptor binding by several orders of magnitude with $K_i$ values <1 nM (24, 27, 28), while compounds 23, 25 and 26 had $K_i\mu$ values of 5–20 nM; however, it should be noted that 25 and 26 were essentially non-selective. Ligand affinity for the μ receptor increased over 1,700-fold with 27 and 28 relative to H-Dmt-Tic-NH₂, a standard prototypic δ-opioid antagonist (Salvadori et al., *Mol. Med.*, 1: 678–689 (1995)). The length of the spacer in the Bid-containing series (23–26) greatly affected the acquisition of high μ affinity (Table IV). Ligand interaction with μ receptors required a definitive distance between aromatic nuclei of Tic and Bid. The chemical and physical nature of the C-terminal substituent, however, plays a role in receptor recognition.

Example 75

This example describes functional pharmacological bioassays.

The in vitro pharmacological assays used a single MVD for δ receptors and a 2- to 3-cm segment of GPI for μ receptors with each suspended in 20 ml organ baths containing balanced salt solutions in a physiological buffer (Salvadori et al., *Mol. Med.*, 1: 678–689 (1995)). Peptide analogues were assayed for μ agonist activity by the inhibition of electrically stimulated contractions in comparison to dermorphin; δ antagonist activity used deltorphin C (δ1-agonist) (Lazarus et al., *Prog. Neurobiol.*, 57: 377–420 (1999)). Data were obtained from 4 independent assays and tissue samples. Agonism is expressed as the IC50 (nM) value and antagonism as pA2 (Labarre et al., *Eur. J. Pharm.*, 406: R1–R3 92000)).

The in vitro pharmacological assays are summarized in Tables IV and V. In Table V, the data are the means of at least four independent experiments. $pA_2$ is measured as: $\log[C-1]/[\text{antagonist}]$, where C is concentration. H-Dmt-Tic-NH—$CH_2$-Bid (24) and H-Dmt-Tic-Gly-NH-Ph (27) exhibited potent δ-agonist activity, in particular compound 24 ($pEC_{50}$=9.90) was greater than that of deltorphin C; its weak μ agonism was nearly two orders of magnitude less than dermorphin. In order to determine if the δ agonist activities of 24 and 27 were mediated by the δ receptor, the $pA_2$ for naloxone was determined using the δ selective agonist deltorphin C. The $pA_2$ values were comparable for all δ agonists confirming that agonist activity in the MVD was mediated by the δ receptor (Table V). Similarly, N,N(Me)$_2$-Dmt-Tic-OH, a highly selective δ antagonist (Salvadori et al., *J. Med. Chem.*, 40: 3100–3108 (1997)), yielded analogous results with deltorphin C and compound 24, while compound 27 had 5-fold lower activity. Thus, the activity of 24 is mediated by δ-opioid receptors, and its δ-agonist activity is more than two orders of magnitude greater than its μ-agonist activity. Interestingly, while compounds 26 and 28 retained potent δ antagonist activity, only 28 had remarkably high μ agonism.

The functional pharmacological activity of compound 23 had an unusual spectrum of behavior that depended on peptide concentration. At low doses, it was possible to estimate δ antagonist activity against deltorphin C, while at high concentration (up to 1 μM), electrical stimulation of the tissue was reduced by 83%.

TABLE IV

In vitro opioid activity of Dmt-Tic analogues.

| | Receptor affinity (nM) | | | Functional Bioactivity | | |
|---|---|---|---|---|---|---|
| | | | | MVD | MVD | GPI |
| compound | $K_i\delta$ | $K_i\mu$ | μ/δ | ($pEC_{50}$) | ($pA_2$) | ($pEC_{50}$) |
| H-Dmt-Tic-OH | 0.022 | 3320 | 150,780 | — | 8.2 | —[a] |
| H-Dmt-Tic-NH$_2$ | 1.22 | 277 | 227 | — | 7.2 | —[a] |
| H-Dmt-Tic-ol | 0.44 | 151 | 344 | — | 7.0 | —[a] |
| H-Dmt-Tic-Ala-NH$_2$ | 0.22 | 47 | 195 | — | 8.0 | —[a] |
| Deltorphin C | 0.21 | 387 | 1840[b] | 9.56 (0.30) | — | — |
| Dermorphin | 82.5 | 0.28 | 0.0034[c] | — | — | 9.15 (0.10) |
| 23 | 0.13 | 7.22 | 7.28 | 7.90 (0.45) | (0.30) | |
| 24 | 0.035 | 0.50 | 14 | 9.90 (0.32) | — | 7.57 (0.14) |
| 25 | 0.067 | 5.49 | 82 | — | 8.32 (0.25) | 6.97 (0.18) |
| 26 | 0.058 | 20.5 | 353 | — | 9.00 (0.29) | 6.45 (0.20) |
| 27 | 0.042 | 0.16 | 3.6 | 8.52 (0.99) | — | 8.59 (0.48) |
| 28 | 0.031 | 0.16 | 5.3 | — | 9.25 (0.3) | 8.57 (0.14) |

—, no activity. [a]Salvadori et al. [b]Lazarus et al. [c]Tomatis et al. [d]Balboni et al.

TABLE V

Pharmacological activity of selected δ agonists/μ agonists.

| | MVD | MVD, antagonist activity ($pA_2$) | |
|---|---|---|---|
| compound | $pEC_{50}$ | naloxone | N,N(CH$_3$)$_2$-Dmt-Tic-OH |
| Deltorphin C | 9.56 | 7.5 | 9.76 |
| 24 | 9.90 | 7.45 | 9.70 |
| 27 | 8.52 | 7.47 | 9.04 |

The results presented in Tables IV and V demonstrate that C-terminal modification of the Dmt-Tic pharmacophore converted a δ antagonist into a pseudopeptide with remarkable new properties. For example, some analogues demonstrated an improvement in μ-opioid affinity and 1-agonist activity with GPI assay as noted previously (see, e.g., Balboni et al., *Peptides*, 21: 1663–1671 (2000)). Benzoimidazole-, pyridoindole- and spiroinden-derivatives of Dmt showed the most interesting properties. Among the benzoimidazole derivatives, 2-amino-1-[3-(1H-benzoimidazole-2-yl)-3,4-dihydro-1H-isoquinoline-2-yl]-3-(4-hydroxyl-2,6-dimethylphenyl)-propane-1-one (FIG. 2, compound 23), showed high δ binding affinity, being 10-fold higher than H-Dmt-Tic-NH$_2$ and 3-fold greater than H-Dmt-Tic-ol. Compound 23 also increased affinity toward the μ receptor nearly 40-fold compared to H-Dmt-Tic-NH$_2$; published data indicated a δ antagonism ($pA_2$, 7.67) and μ agonist activities (IC$_{50}$, 30 nM) (Balboni, supra). This observation was substantiated with the functional bioassays of newly synthesized preparations of 23 that revealed δ-antagonist (pA$_2$, 7.90) and δ-agonist activities (pEC$_{50}$, 7.28) (Table IV). All previously described Dmt-Tic analogues are all δ antagonists (Lazarus et al., *Drug Discovery Today*, 3: 284–294 (1998); Bryant et al., *Trends Pharmacol. Sci.*, 19: 42–46 (1998)), although hydrophobic and aromatic substituents at the C-terminus provided evidence that they substantially modified the properties of the Dmt-Tic pharmacophore.

The data clearly demonstrate that a third pharmacophore, namely 1-H-benzimidazol-2-yl (Bid), in lieu of the carboxylic acid function of H-Dmt-Tic-OH or in analogues containing a linker in the general formula H-Dmt-Tic-X-Bid, is generally better than N-phenyl amide to elicit δ agonist or antagonist activities (compare 25 or 26 to 28). Interestingly, H-Dmt-Tic-Gly-NH-Ph (27) had essentially equivalent activity as a δ agonist and a μ agonist. However, replacing the N-phenyl amide (27) with a N-benzyl amide (28) function not only increased the distance between aromatic nuclei, but also converted the analogue into a potent δ antagonist with excellent μ-agonist activity, although about one-fourth of that for dermorphin.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound of formula:

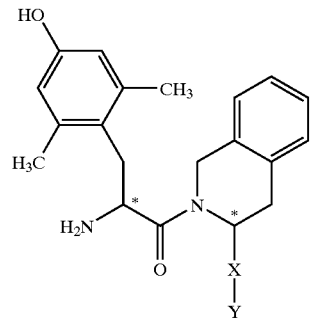

wherein X is a spacer comprising at least one amino acid residue, and Y comprises a benzoimidazolyl group.

2. A compound of formula:

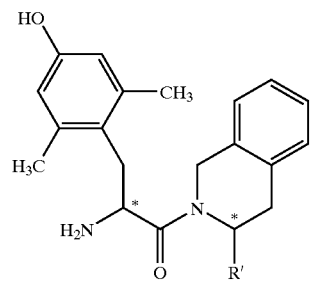

wherein R' is selected from the group consisting of

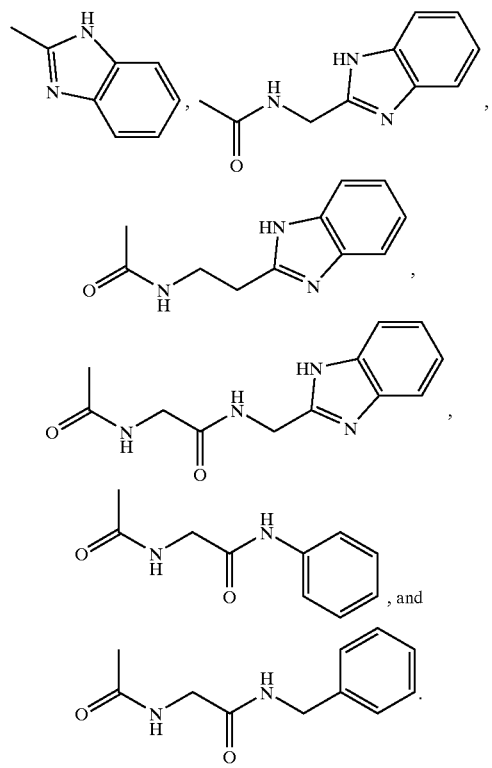

3. A composition comprising at least one compound of claim 1 and a carrier.

4. A composition comprising at least one compound of claim 2 and a carrier.

5. A method of antagonizing a δ-opioid receptor in a mammal in need thereof, which method comprises administering at least one compound of formula:

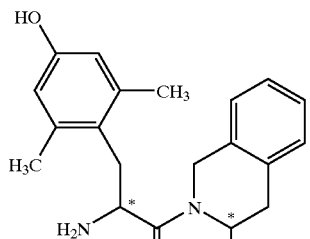

wherein R' is selected from the group consisting of:

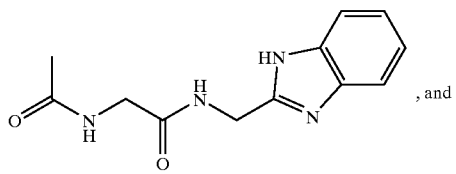
, and

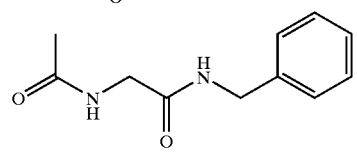

in an amount that antagonizes the δ-opioid receptor in said mammal, whereupon the δ-opioid receptor in said mammal is antagonized.

6. The method of claim 5, wherein the compound is administered in an amount that also agonizes a μ-opioid receptor in said mammal.

7. A method of agonizing a δ-opioid receptor in a mammal in need thereof, which method comprises administering at least one compound of formula:

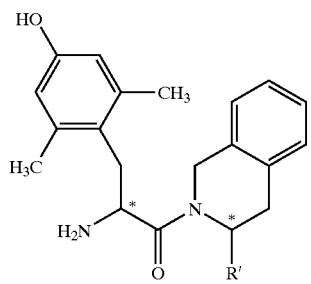

wherein R' is

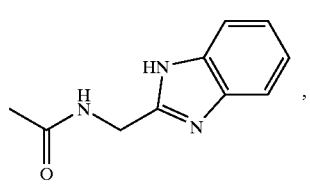
,

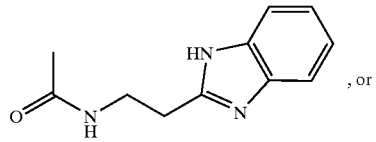
, or

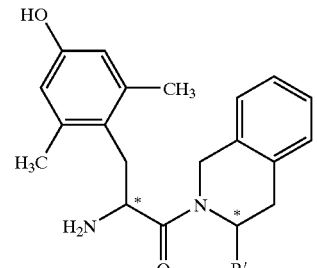

in an amount that agonizes the δ-opioid receptor in said mammal, whereupon the δ-opioid receptor in said mammal is agonized.

8. A method of agonizing a μ-opioid receptor in a mammal in need thereof, which method comprises administering at least one compound of formula:

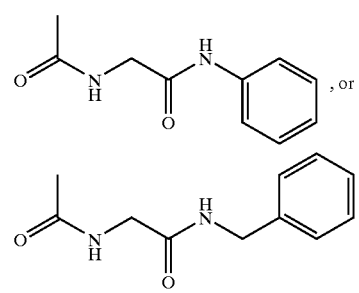

wherein R' is

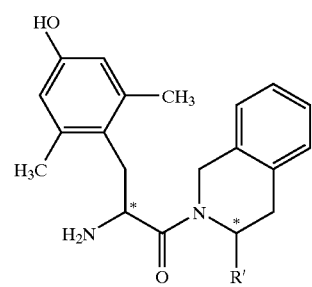
, or

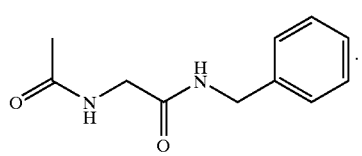

in an amount that agonizes the μ-opioid receptor in said mammal, whereupon the μ-opioid receptor in said mammal is agonized.

9. A compound of formula:

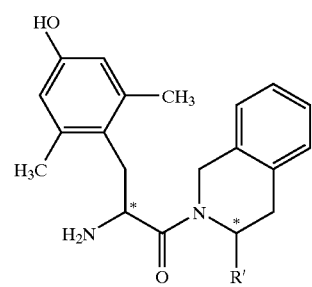

wherein R' is

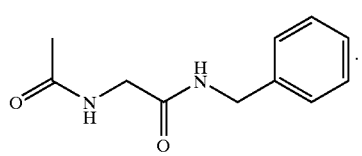
.

10. A method of antagonizing a δ-opioid receptor and agonizing a μ-opioid receptor in a mammal in need thereof, which method comprises administering the compound of claim 9 in an amount that antagonizes the δ-opioid receptor and agonizes the μ-opioid receptor in said mammal, whereupon the δ-opioid receptor is antagonized and the μ-opioid receptor is agonized in said mammal.

* * * * *